US010861583B2

(12) United States Patent
Jessen

(10) Patent No.: US 10,861,583 B2

(45) Date of Patent: Dec. 8, 2020

(54) SYSTEMS AND METHODS FOR BIOMARKER IDENTIFICATION

(71) Applicant: Laboratory Corporation of America Holdings, Burlington, NC (US)

(72) Inventor: Walter Joseph Jessen, New Palestine, IN (US)

( * ) Notice: Subject to any disclaimer, the term of this patent is extended or adjusted under 35 U.S.C. 154(b) by 95 days.

(21) Appl. No.: 15/977,000

(22) Filed: May 11, 2018

(65) Prior Publication Data

US 2019/0065665 A1 Feb. 28, 2019

Related U.S. Application Data

(60) Provisional application No. 62/523,382, filed on Jun. 22, 2017, provisional application No. 62/505,536, filed on May 12, 2017.

(51) Int. Cl.

*G16B 5/00* (2019.01)

*C12Q 1/6886* (2018.01)

(Continued)

(52) U.S. Cl.

CPC ............. *G16B 5/00* (2019.02); *C12Q 1/6886* (2013.01); *G06F 16/215* (2019.01);

(Continued)

(58) Field of Classification Search

CPC .......... G16B 5/00; G16B 40/00; G16B 50/00; G06F 16/215; G06F 16/2465; G06F 16/9024; C12Q 1/6886

(Continued)

(56) References Cited

U.S. PATENT DOCUMENTS 8,600,718 B1 * 12/2013 Stepaniants ............ G16B 20/00 703/11

8,788,444 B2 * 7/2014 Ball ..................... C12Q 1/6886 706/25

(Continued)

FOREIGN PATENT DOCUMENTS

| | | |
|---|---|---|
| EP | 2360279 | 8/2011 |
| WO | 2004001060 | 12/2003 |

OTHER PUBLICATIONS

Faiola et al., "Gene Expression Profile in Bone Marrow and Hematopoietic Stem Cells in Mice Exposed to Inhaled Benzene", Mutation Research, vol. 549, Issue 1-2, May 15, 2004, pp. 195-212.

(Continued)

*Primary Examiner* — Evan Aspinwall

(74) *Attorney, Agent, or Firm* — Kilpatrick Townsend & Stockton LLP

(57) ABSTRACT

The present invention relates to systems and methods for identifying a biomarker from associative and knowledge based systems and processes. Particularly, aspects of the present invention are directed to a computer implemented method that includes data mining one or more public sources of biomedical text, scientific abstract, or bioinformatic data using queries to identify database terms associated with one or more predetermined terms, scoring association(s) between each of the identified database terms and the one or more predetermined terms, determining a subset b based on the score of the association(s), developing an interaction network model comprising the database terms in subset b, interactions, and additional database terms using a combination of algorithms in a predetermined order, and identifying candidate biomarkers from the interaction network model based on a ranking of the database terms in subset b (Continued)

and the additional database terms in the interaction network model.

26 Claims, 15 Drawing Sheets

(51) Int. Cl.
*G16B 50/00* (2019.01)
*G06F 16/215* (2019.01)
*G06F 16/2458* (2019.01)
*G06F 16/901* (2019.01)
*G16B 40/00* (2019.01)

(52) U.S. Cl.
CPC ...... *G06F 16/2465* (2019.01); *G06F 16/9024* (2019.01); *G16B 40/00* (2019.02); *G16B 50/00* (2019.02)

(58) Field of Classification Search
USPC .......................................................... 707/692
See application file for complete search history.

(56) References Cited

U.S. PATENT DOCUMENTS

2006/0241869 A1* 10/2006 Schadt ................. C12Q 1/6883 702/19
2007/0072226 A1* 3/2007 Chen ........................ G16B 5/00 435/6.13
2010/0239656 A1* 9/2010 Astsaturov ........... C12Q 1/6886 424/450
2012/0258874 A1* 10/2012 Narain ..................... G16B 5/00 506/8
2014/0172398 A1* 6/2014 Hoeng ................... G06N 7/005 703/11
2015/0220838 A1* 8/2015 Martin ..................... G06N 5/04 706/12
2019/0024173 A1* 1/2019 Lee ........................ G16H 50/30
2019/0072541 A1* 3/2019 Christiano ........... G01N 33/564
2019/0078093 A1* 3/2019 Domenyuk .......... C12N 15/115
2019/0085324 A1* 3/2019 Regev .................. C12Q 1/6886

OTHER PUBLICATIONS

Mesaros et al., "Bioanalytical Techniques for Detecting Biomarkers of Response to Human Asbestos Exposure", Bioanalysis, vol. 7, Issue 9, May 1, 2015, pp. 1157-1173.
PCT/US2018/032187 , "International Search Report and Written Opinion", dated Sep. 4, 2018, 13 pages.
PCT/US2018/032293 , "International Search Report and Written Opinion", dated Sep. 11, 2018, 18 pages.
Risom et al., "Oxidative DNA Damage and Defence Gene Expression in the Mouse Lung After Short-Term Exposure to Diesel Exhaust Particles by Inhalation", Carcinogenesis, vol. 24, Issue 11, Jun. 19, 2003, pp. 1847-1852.
Robertson et al., "The Cellular and Molecular Carcinogenic Effects of Radon Exposure: A Review", International Journal of Molecular Sciences, vol. 14, Issue 7, Jul. 5, 2013, pp. 14024-14063.
Tothill et al., "Massively-Parallel Sequencing Assists the Diagnosis and Guided Treatment of Cancers of Unknown Primary", The Journal of Pathology, vol. 231, Issue 4, Dec. 1, 2013, pp. 413-423.
Landschulz, K. and Jessen, W., "Modeling NAFLD/NASH Biology to Identify Candidate Biomarkers Linked to miRNA-103 Targets," presented May of 2016.
Jessen, W. et al., "Connecting Alzheimer's Disease, Parkinson's Disease, and Type 2 Diabetes Through Disease Network models and Enrichment Analysis," Covance, Indiana University School of Dentistry, presented Mar. of 2015.
Jessen, W., "Network Modeling of Protein-Protein Interactions to Identify and Prioritize Candidate Biomarkers," Covance Solutions Made Real, presented Jun. of 2014.
PCT/US2018/032293 , "International Preliminary Report on Patentability", dated Nov. 21, 2019, 12 pages.

* cited by examiner

200

205

| index | Symbol | Description | Aliases | Rank | protein_coding | non_coding | pseudo gene | annotated gene | alternatively_spliced | Direct association | OMIM ID | Entrez Gene ID | other_designations |
|---|---|---|---|---|---|---|---|---|---|---|---|---|---|
| 7 | BTK | Bruton tyrosine kinase | AGMX1, AT, ATK, BPK, IMD1, PSCTK1, XLA | | True | False | False | True | True | False | 300300 | 695 | B-cell progenitor kinase\|Bruton agammaglobulinemia tyrosine kinase\|Bruton's tyrosine kinase\|agammaglobulinaemia tyrosine... |
| 8 | CARD11 | caspase recruitment domain family member 11 | BENTA, BIMP3, CARMA1, IMD11, PPBL | | True | False | False | True | True | False | 607210 | 84433 | CARD-containing MAGUK protein 1\|bcl10-interacting maguk protein 3\|carma 1\|caspase recruitment domain family, member 11 |
| 9 | CD247 | CD247 molecule | CD3-ZETA, CD3H, CD3Q, CD3Z | | True | False | False | True | True | False | 186780 | 919 | CD247 antigen, zeta subunit\|CD3Z antigen, zeta polypeptide (TiT3 complex)\|CD3zeta chain\|T-cell antigen receptor complex... |
| 10 | CD3D | CD3d molecule | CD3-DELTA, IMD19, T3D | | True | False | False | True | True | False | 186790 | 915 | CD3 antigen, delta subunit\|CD3 delta\|CD3d antigen, delta polypeptide (TiT3 complex-)\|CD3d molecule, delta (CD3-TCR complex... |
| 11 | CD3E | CD3e molecule | IMD18, T3E, TCRE | | True | False | False | True | False | False | 186830 | 916 | CD3-epsilon\|CD3e antigen, epsilon polypeptide (TiT3 complex)\|CD3e molecule, epsilon (CD3-TCR complex)\|T-cell antigen receptor... |
| 12 | CD3G | CD3g molecule | CD3-GAMMA, IMD17, T3G | | True | False | False | True | True | False | 186740 | 917 | CD3g antigen, gamma polypeptide (TiT3 complex)\|CD3g molecule, epsilon (CD3-TCR complex)\|CD3g molecule, gamma (CD3-TCR... |
| 13 | CD4 | CD4 molecule | CD4mut | 2 | True | False | False | True | True | True | 186940 | 920 | CD4 antigen (p55)\|CD4 receptor\|T-cell surface antigen T4/Leu-3 |
| 14 | CHUK | conserved helix-loop-helix ubiquitous kinase | IKBKA, IKK-ALPHA, IKK1, NFKBIKA, TCF16 | | True | False | False | True | True | False | 600664 | 1147 | I-kappa-B kinase 1\|I-kappa-B kinase-alpha\|IKK-a kinase\|IkB kinase alpha subunit\|Nuclear factor NFkappaB inhibitor kinase... |
| 15 | CXCL10 | C-X-C motif chemokine ligand 10 | C7, IFI10, IP-10, SCYB10, crg-2, gIP-10, mob-1 | 2 | True | False | False | True | False | True | 147310 | 3627 | 10 kDa interferon gamma-induced protein\|chemokine (C-X-C motif) ligand 10\|gamma IP10\|gamma-IP10\|interferon... |
| 16 | CXCL8 | C-X-C motif chemokine ligand 8 | GCP-1, GCP1, IL8, LECT, LUCT, LYNAP, MDNCF, MONAP, ... | 2 | True | False | False | True | False | True | 146930 | 3576 | T-cell chemotactic factor\|alveolar macrophage chemotactic factor I\|beta endothelial cell-derived neutrophil activating peptide\|beta-... |

FIG. 2

SYSTEMS AND METHODS FOR BIOMARKER IDENTIFICATION

CROSS REFERENCE TO RELATED APPLICATIONS

The present application claims priority and benefit from U.S. Provisional Application No. 62/523,382, filed Jun. 22, 2017, entitled "SYSTEMS AND METHODS FOR BIOMARKER IDENTIFICATION" and U.S. Provisional Application No. 62/505,536, filed May 12, 2017, entitled "SYSTEMS AND METHODS FOR BIOMARKER IDENTIFICATION," the entire contents of which are incorporated herein by reference for all purposes.

FIELD OF THE INVENTION

The present invention relates to systems and methods for biomarker identification, and in particular to systems and methods for identifying a biomarker from associative and knowledge based systems and processes.

BACKGROUND

The term "biomarker" generally refers to any substance, structure, or process that can be measured reflecting a response between a biological system and a potential hazard, which may be chemical, physical, or biological. The measured response may be functional and physiological, biochemical at the cellular level, or a molecular interaction. Examples of biomarkers include everything from pulse and blood pressure through basic chemistries to more complex laboratory tests of blood and other tissues. Traditional medical signs such as pulse and blood pressure have a long history of use in clinical practice and today's biomarkers such as tumor markers for cancer are merely an objective, quantifiable medical sign that modern laboratory science allows us to measure reproducibly. The use of biomarkers, and in particular molecular or gene biomarkers, is somewhat newer, and the best approaches to this practice are still being developed and refined. The key issue is determining the relationship between any given measurable biomarker and a potential hazard such as a particular disease condition.

In order to improve upon conventional techniques for identifying biomarkers, a primary goal for researchers has been to optimize genome-wide screening for molecular biomarkers especially with high-throughput techniques, perform differential analysis based on different types of omics data, and interpret omics data using bioinformatics. In particular, the accumulation of various kinds of '-omics' (e.g. genomics, transcriptomics and proteomics) data enables one to identify potential molecular biomarkers that can predict disease risks and/or confirm disease onset and progression. Although the molecular biomarkers identified based on the omics data achieve some success, most of the molecular biomarkers are not reliable and have low reproducibility, where the biomarkers identified from one dataset sometimes fail to work in another dataset for the same disease. This phenomenon arises since many diseases, especially complex diseases, are well recognized as the results of dysregulation of biological systems instead of the mutations of individual genes, whereas the molecular biomarkers are generally assumed to be functionally independent of each other. Accordingly, the need exists for improved techniques for high precision biomarker identification.

BRIEF SUMMARY

In various embodiments, a computer implemented method is provided for that includes data mining one or more public sources of biomedical text, scientific abstract, or bioinformatic data using queries to identify database terms associated with one or more predetermined terms, scoring association(s) between each of the identified database terms and the one or more predetermined terms, determining a subset b based on the score of the association(s) between each of the identified database terms and the one or more predetermined terms, developing an interaction network model comprising the database terms in subset b, interactions, and additional database terms using a combination of algorithms in a predetermined order, and identifying candidate biomarkers from the interaction network model based on a ranking of the database terms in subset b and the additional database terms in the interaction network model. The interaction network model may be developed with preset parameters including a tissue or organ specific parameter, which restricts the interactions and the additional database terms to a specific tissue or organ.

In accordance with some aspects, the computer implemented method further includes scrubbing the identified database terms to remove alleged database terms that are not "actual" database terms of interest to generate a subset a that includes only "actual" database terms of interest, and generating a list of the subset b that includes a name of the identified database terms, identifiers or symbols of the identified database terms, and the score of the association(s) between each identified database term and the one or more predetermined terms.

In some embodiments, the developing the interaction network model includes: applying a growth algorithm to the database terms in subset b to build 5-50 nodes upstream including the additional database terms, wherein correlation and expression relationships are excluded in the growth algorithm, applying a growth algorithm to the database terms in subset b to build 5-50 nodes downstream including the additional database terms, wherein the correlation and expression relationships are excluded in the growth algorithm, connecting all nodes that can be directly connected given presets parameters using a direct connection algorithm to create a core network, wherein the correlation and expression relationships are excluded in the direct connection algorithm, applying Dijkstra's shortest paths algorithm to the core network to identify direct connections and connections where there is one additional step, wherein the correlation and expression relationships are excluded in the Dijkstra's shortest paths algorithm, applying a direct connection algorithm to all nodes in the core network that can be directly connected given the preset parameters, wherein the correlation and expression relationships are excluded in the direct connection algorithm, and applying the Dijkstra's shortest paths algorithm to the core network to identify direct connections and connections where there is one additional step, wherein the correlation and expression relationships are included in the Dijkstra's shortest paths algorithm.

In accordance with other aspects, the computer implemented method further includes identifying an intersection between a first data set and a second data set, wherein the first data set includes a list of the database terms in subset b and the additional database terms from the interaction network model and a list of known test analytes having existing validated assays; and ranking the database terms in subset b and the additional database terms as the candidate biomarkers based on criteria including the intersection between the first data set and the second data set.

Optionally, the criteria includes: Rank 1 candidate biomarkers, which are those database terms independently recommended by one or more therapeutic experts or published industry guidance as a "biomarker"; Rank 2 candidate biomarkers, which are those database terms such as genes or proteins identified by the data mining and a component of the interaction network model; and Rank 3 candidate biomarkers, which are those database terms that are not Rank 1 or Rank 2 candidate biomarkers.

Optionally, the method further comprises identifying one or more additional terms to be associated with the one or more predetermined terms that were not found in the data mining, and importing the one or more additional terms into subset b. The interaction network model may comprise the database terms and the one or more additional terms in subset b, interactions, and additional database terms. In certain embodiments, the one or more additional terms include chemicals or small molecules involved in one or more biological pathways comprising the database terms.

In other embodiments, a non-transitory machine readable storage medium is provided for having instructions stored thereon that when executed by one or more processors cause the one or more processors to perform a method including data mining one or more public sources of biomedical text, scientific abstract, or bioinformatic data using queries to identify database terms associated with one or more predetermined terms, scoring association(s) between each of the identified database terms and the one or more predetermined terms, scrubbing the identified database terms to remove alleged database terms that are not "actual" database terms of interest to generate a subset a that includes only "actual" database terms of interest, determining a subset b of the subset a based on the score of the association(s) between each of the identified database term and the one or more predetermined terms, developing an interaction network model comprising the database terms in subset b, interactions, and additional database terms using a combination of algorithms in a predetermined order, and identifying candidate biomarkers from the interaction network model based on a ranking of the database terms in subset b and the additional database terms in the interaction network model. The interaction network model may be developed with preset parameters including a tissue or organ specific parameter, which restricts the interactions and the additional database terms to a specific tissue or organ.

In yet other embodiments, a system is provided for that includes one or more processors and non-transitory machine readable storage medium, program instructions to data mine one or more public sources of biomedical text, scientific abstract, or bioinformatic data using queries to identify database terms associated with one or more predetermined terms, program instructions to score association(s) between each of the identified database terms and the one or more predetermined terms, program instructions to scrub the identified database terms to remove alleged database terms that are not "actual" database terms of interest to generate a subset a that includes only "actual" database terms of interest, program instructions to determine a subset b of the subset a based on the score of the association(s) between each of the identified database term and the one or more predetermined terms, program instructions to develop an interaction network model comprising the database terms in subset b, interactions, and additional database terms using a combination of algorithms in a predetermined order, and program instructions to identify candidate biomarkers from the interaction network model based on a ranking of the database terms in subset b and the additional database terms in the interaction network model. The program instructions are stored on the non-transitory machine readable storage medium for execution by the one or more processors. The interaction network model may be developed with preset parameters including a tissue or organ specific parameter, which restricts the interactions and the additional database terms to a specific tissue or organ.

BRIEF DESCRIPTION OF THE DRAWINGS

The present invention will be better understood in view of the following non-limiting figures, in which:

FIG. 2 shows an exemplary list of database terms in the subset b in accordance with some aspects of the invention;

DETAILED DESCRIPTION

I. Introduction

In various embodiments, the present invention is directed to a method for identifying a biomarker from associative and knowledge based systems and processes. Conventional approaches for identifying molecular biomarkers generally detect differentially expressed genes by setting a threshold, where those genes whose expression changes above the threshold are used as molecular biomarkers to the genome/transcriptome or performing a full de-novo assembly of those sequencing reads. Unfortunately, the noise inherited in the gene expression data makes it a challenging task to detect reliable differentially expressed genes with such an arbitrarily set threshold. Therefore, statistical techniques have been proposed to detect more reliable differential genes, e.g. the nonparametric approach and the empirical Bayesian method, where most of the approaches are based on statistical tests. These approaches, however, are both too time consuming and the biomarkers identified from one dataset sometimes fail to work in another dataset for the same disease.

To address these problems, the present invention is directed to systems and methods that implement both associative and knowledge based systems and processes to identify one or more biomarkers. For example, one illustrative embodiment of the present disclosure is directed to a computer implemented method that includes data mining one or more public sources of biomedical text, scientific abstract, or bioinformatic data using queries to identify database terms associated with one or more predetermined terms, scoring association(s) between each of the identified database terms and the one or more predetermined terms, determining a subset b based on the score of the association(s) between each of the identified database term and the one or more predetermined terms, developing an interaction network model comprising the database terms in subset b using a combination of algorithms in a predetermined order, and identifying candidate biomarkers from the interaction network model based on a ranking of the database terms in the interaction network model.

While some embodiments are disclosed herein with respect to identifying molecular biomarkers, this is not intended to be restrictive. In addition to identifying molecular biomarkers, the teachings disclosed herein can also be applied to other biomarkers that can be measured reflecting a response between a biological system and a potential hazard, which may be chemical, physical, or biological. For example, cellular or biochemical biomarkers, e.g., prostate-specific antigen, creatine kinase, dystrophin protein, etc. could be identified as determinative of the state of an individual's health, disease onset and progression; or whether an experimental treatment is working or not.

II. Techniques for Identifying a Biomarker

Figure 1:
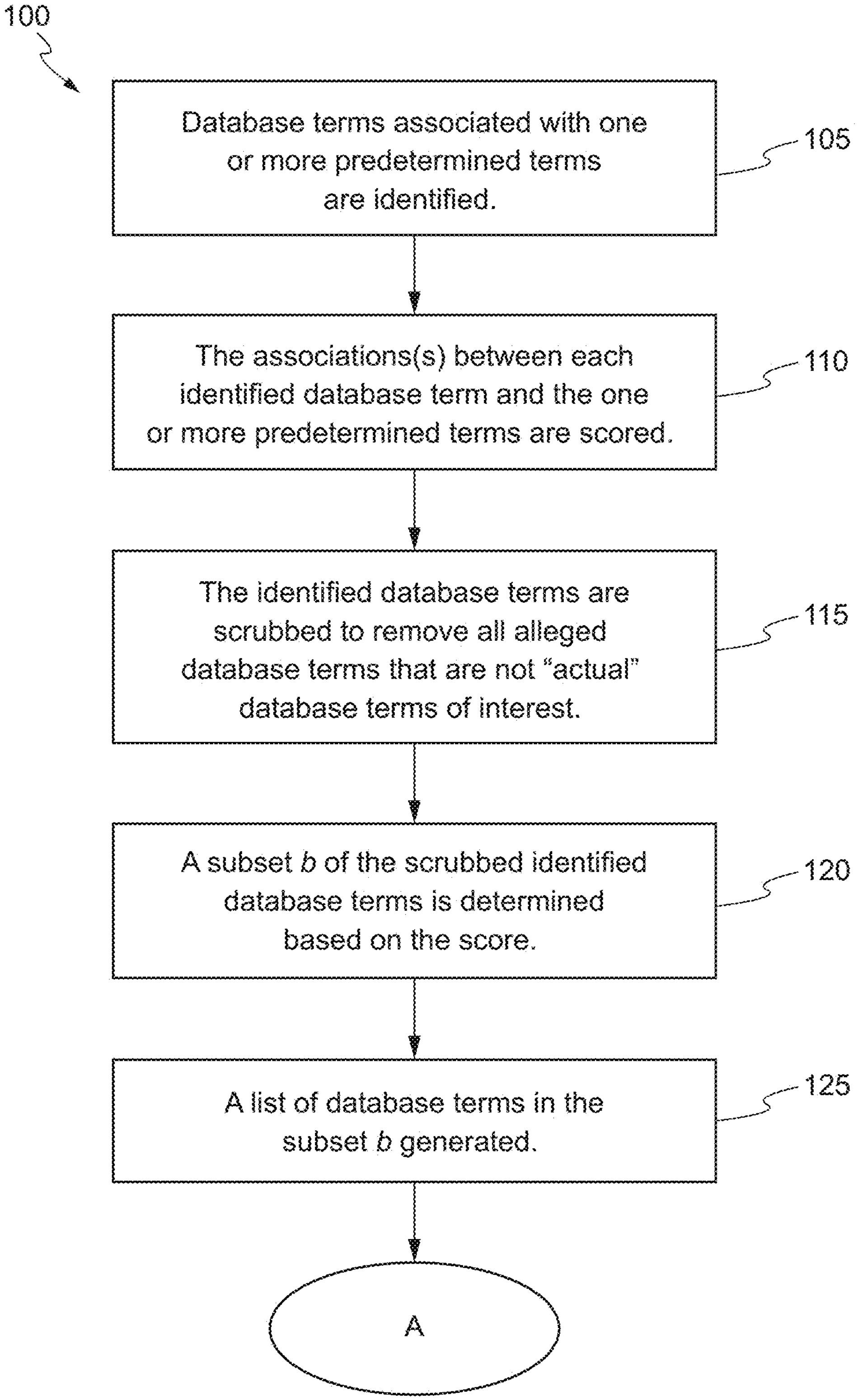
FIG. 1 shows an exemplary flow for identifying a biomarker using associative (e.g., gene/protein-disease or gene/protein-term associations) based systems and processes in accordance with various aspects of the invention.
Figure 3:
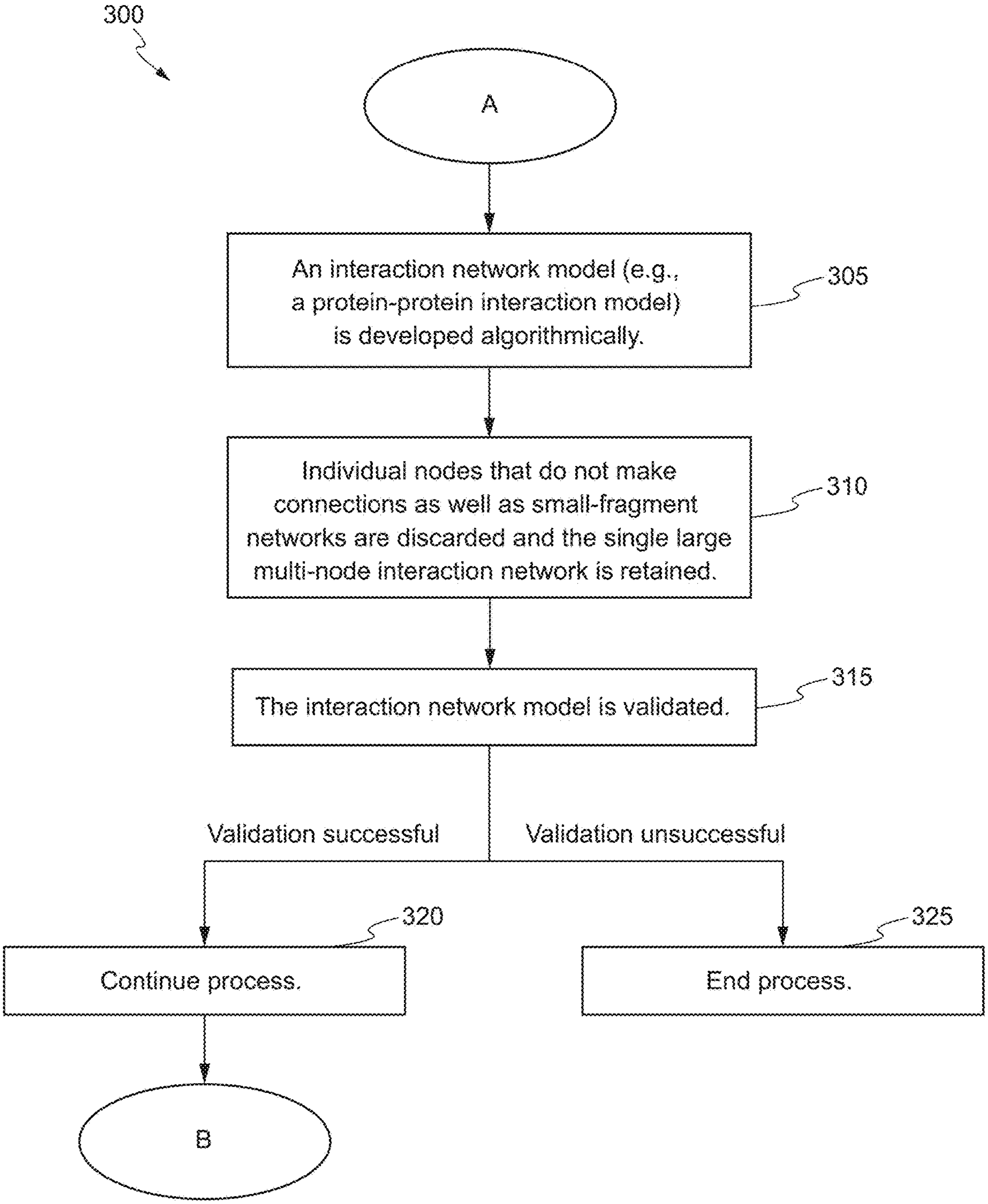
FIG. 3 shows an exemplary flow for identifying a biomarker using knowledge based systems and processes in accordance with various aspects of the invention.
Figure 5:
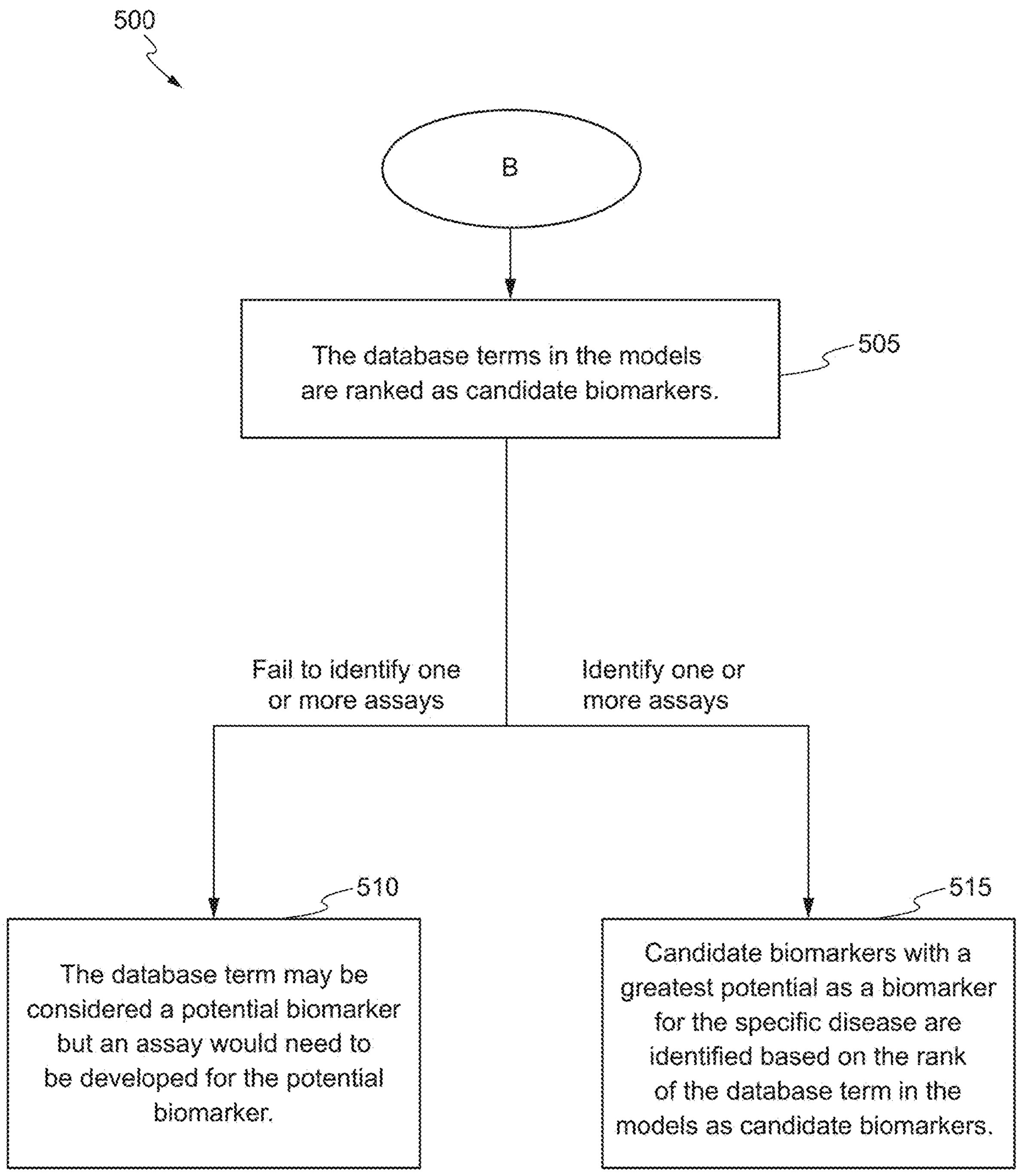
FIG. 5 shows an exemplary flow for biomarker analysis in accordance with various aspects of the invention.

FIGS. 1, 3, and 5 depict simplified flowcharts depicting processing performed for identifying a biomarker according to embodiments of the present invention. The steps of FIGS. 1, 3, and 5 may be implemented in the system environment of FIG. 6, for example. As noted herein, the flowcharts of FIGS. 1, 3, and 5 illustrate the architecture, functionality, and operation of possible implementations of systems, methods, and computer program products according to various embodiments of the present invention. In this regard, each block in the flowchart or block diagrams may represent a module, segment, or portion of code, which comprises one or more executable instructions for implementing the specified logical functions. It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combination of blocks in the block diagrams and/or flowchart illustration, can be implemented by special purpose hardware-based systems that perform the specified functions or acts, or combinations of special purpose hardware and computer instructions.

FIG. 1 depicts a simplified flowchart 100 illustrating a process for identifying a biomarker using associative (e.g., gene/protein-disease or gene/protein-term associations) based systems and processes. At step 105, one or more public sources of biomedical text (e.g., peer reviewed literature), scientific abstract, or bioinformatic data is data mined using queries to identify database terms (e.g., a protein, a gene, a biochemical, a cellular component, other biomolecules such as portions of genes, non-coding portions of genes, siRNAs, miRNAs, hormones, steroids, peptides, etc.) associated with one or more predetermined terms (i.e., query terms). The one or more predetermined terms may be query terms for a specific disease of interest such as lung cancer and/or a risk factor for a disease of interest such as tobacco smoke. In certain embodiments, a query is generated using a web server, such as web-based tool called PolySearch, in order to identify and enumerate R1, R2, R3 and R4 sentences (R stands for relevancy) within the one or more public sources of biomedical text that include one or more of the "query terms", "association words", and "database terms."

For example, an R4 sentence may be a sentence that contains just one of the database terms and is used only for statistical normalization. An R3 sentence may be a sentence that has one of the database terms as well as the query term. An R2 sentence may be a sentence that has one of the database terms, one of the query terms, as well as at least one association word. An R1 sentence may be the same as an R2 sentence but in addition, an R1 sentence may have to pass pattern recognition criteria. Example association words may include words that develop an association between a query term and a database term, for example: patients, treatment, risk, associated, role, antigen, association, autosomal, biomarker, cause, caused, decline, deficiency, deficient, deleted, diagnosed, diagnosis, dominant, elevate, etc. However, one skilled in the art will understand that modifications of this identification and enumeration process may be acceptable provided that the modifications do not change the primary goal of identifying a biomarker using associative based systems and processes, and may include, without limitation, modifications that involve similar steps to the afore-mentioned process and/or involve the reduction or addition of steps (e.g., only using R3 sentences (occurrence of both the database term and query term).

At step 110, the association(s) between each identified database term and the one or more predetermined terms is scored. For example, relevancy rules and pattern recognition may be utilized within sentences, paragraphs, or abstracts that include an identified database term such as gene or protein and/or the one or more predetermined terms to score the strength of an association. In some embodiments, the scoring is performed using pattern recognition to identify "query term"-"association word"-"database term" patterns, where a defined number of words (e.g., distance) is between the "query word" and the "association word" and/or a defined number of words (e.g., distance) is between the "query word", the "association word", and the "database term". In certain embodiments, the score is the sum of association values calculated for each of the R1, R2, R3 and R4 sentences collectively. For the purposes of generating the score and calculating individual association values, R1 sentences may be given a value of, for example 50, R2 sentences may be given a value of, for example 25, R3 sentences may be given a value of, for example 5, and R4 sentences may be given a value of, for example 1. The association values provided for each type of sentence are weights that can be tuned to provide greater precision for identifying a biomarker.

At step 115, the identified database terms are scrubbed to remove alleged database terms that are not "actual" database terms of interest (e.g., a "false positive" result from the queries) to generate a subset a that includes only "actual" database terms of interest, for example verified genes or proteins. In certain embodiments, the scrubbing includes mapping database terms such as genes or protein names to gene or protein identifiers and symbols using a mapping application. Data curation may be performed on those genes or proteins that fail to be mapped by the mapping application to remove all alleged genes or proteins that are not "actual" genes or proteins.

At step 120, a subset b of the subset a of identified and scrubbed database terms is determined based on the score of the association(s) between each identified database term and the one or more predetermined terms. For example, the subset b may be determined by assigning a score threshold to isolate the top 30, 50, 75, or 100, database terms identified as being associated with the one or more predetermined terms (i.e., those genes or proteins with the highest scored association(s)). The purpose is to identify 30-100 high-scoring associations between query terms and database terms that can be used as seeds to construct indication models described with respect to FIG. 3.

At step 125, a list of all the database terms in the subset b is generated. In certain embodiments, the list includes the name of the database terms such as the names of genes or proteins, the identifiers or symbols of the genes or proteins, and the score of the association(s) between each identified gene or protein and the one or more predetermined terms. FIG. 2 depicts an exemplary list 200 of database terms 205 in the subset b in accordance with various aspects of the present invention. In certain embodiments, the process further comprises identifying one or more additional terms to be associated with the one or more predetermined terms that were not found in the data mining, and importing the one or more additional terms into subset b. For example, an expert or scientist in the field may provide the one or more additional terms based on prior knowledge or the one or more additional terms may be founding using a database query (e.g., an intranet query or a web query) different from the query performed in step 105. In certain embodiments, the one or more additional terms include chemicals or small molecules involved in one or more biological pathways comprising the database terms.

FIG. 3 depicts a simplified flowchart 300 illustrating a process for identifying a biomarker using knowledge based systems and processes. At step 305, an interaction network model (e.g., a gene/protein-gene/protein interaction model) comprising the database terms in subset b, interactions, and additional database terms is developed using a combination of algorithms in a predetermined order such as Dijkstra's shortest path algorithm (or a similar algorithm for finding the shortest paths between nodes), direct connection algorithm (e.g., an algorithm that identifies direct connections between existing nodes in the network), a growth algorithm, etc. In certain embodiments, interactions and the database terms (e.g., genes/proteins) added to the network are restricted to a given tissue, set of tissues (e.g., lung tissue), or organ (e.g., kidney) relevant for the one or more predetermined terms being modeled. Specifically, pairs of genes or proteins in the subset b are selected and one or more tissue/organ specific genes or proteins that directly interact with both genes or proteins of the pair may be identified. Identification of the direct interactions may be based on peer-reviewed study data and specify a direction, mechanism and effect of the one or more tissue/organ specific genes or proteins on both of the genes or proteins of the pair. These "subnetworks of genes or proteins" are repeatedly constructed algorithmically to form a large multi-node gene/protein-gene/protein interaction network.

In various embodiments, an interaction network model (e.g., a gene/protein-gene/protein interaction model) is developed with preset parameters, e.g., a tissue/organ specific parameter and an exclude indirect interactions parameter. Initially, a growth algorithm may be applied to the database terms in subset b to build 5-50 nodes, e.g., 25 nodes, including the additional database terms such as genes/proteins upstream (exclude correlation and expression relationships). Additionally, a growth algorithm may be applied to the database terms in subset b to build 5-50 nodes, e.g., 25 nodes, including the additional database terms such as genes/proteins downstream (exclude correlation and expression relationships). Thereafter, a direct connection algorithm (e.g., an algorithm that identifies direct connections between existing nodes in the network) may be used to connect all nodes that can be directly connected given the presets parameters (exclude correlation and expression relationships). This process creates a core network based on database terms associated with the disease or query terms being modeled (i.e., from the data mining) along with tissue/organ specific connections and nodes that interact with those database terms. Essentially these steps build a "neighborhood" of additional database terms or gene/protein interactions around the database terms or genes/proteins identified previously as being highly associated with the disease or query terms (i.e., from data mining discussed with respect to FIG. 1).

Once the core network is created, Dijkstra's shortest paths algorithm (or a similar algorithm for finding the shortest paths between nodes) may be applied to identify direct connections and connections where there is one additional step (exclude correlation and expression relationships). Thereafter, the direct connection algorithm may be applied to connect all nodes that can be directly connected given the preset parameters (exclude correlation and expression relationships). Thereafter, Dijkstra's shortest paths algorithm (or a similar algorithm for finding the shortest paths between nodes) may be applied to identify direct connections and connections where there is one additional step (include correlation and expression relationships). The exclusion of the correlation and expression relationships allows for greater model relevancy as only direct, physical connections are identified. While the inclusion of the correlation and expression relationships during the final step of the process allows for sensitivity to emerging biomarkers with undetermined physical interactions to other nodes in the model.

Figure 4:
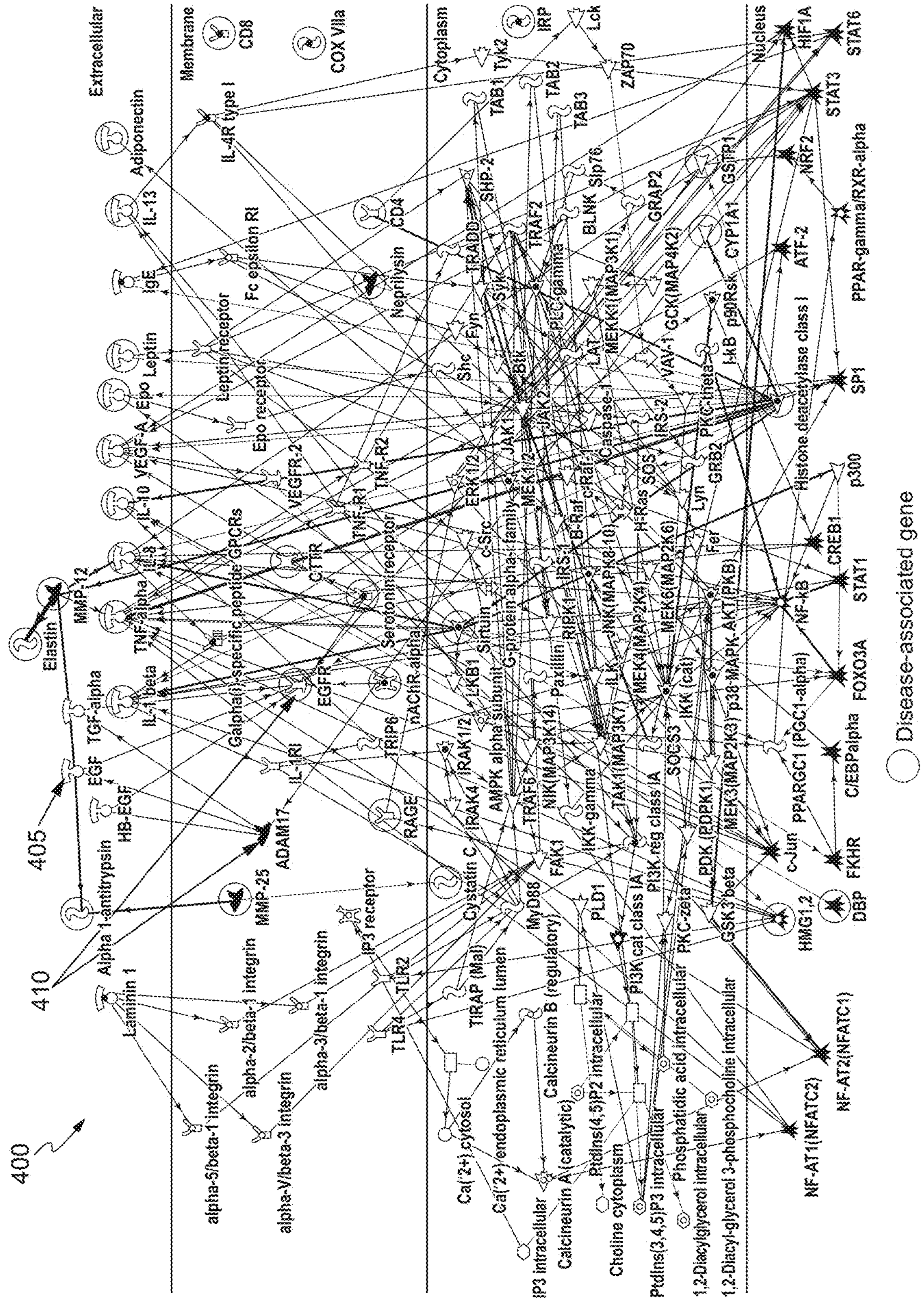
FIG. 4 shows an exemplary multi-node interaction network in accordance with various aspects of the invention.

At step 310, individual nodes that do not make connections as well as small-fragment networks are discarded and the single large multi-node interaction network is retained. FIG. 4 depicts an exemplary multi-node interaction network 400 including one or more tissue/organ specific genes or proteins 405 that directly interact with both genes or proteins of each identified pair 410 in accordance with various aspects of the present invention. At step 315, the interaction network model is validated to ensure it accurately simulates disease biology. In certain embodiments, the validation may be performed using statistics to demonstrate enrichment (e.g., significant over-representation) of the database terms in subset b and the additional database terms such as genes/proteins from the interaction network model in an independent third party data source that comprises human gene-disease associations. This may be done using a hypergeometric test to obtain an enrichment P-value for the model gene list against a disease gene list cataloged in the third party data source.

At step 320, if the interaction network model can be statistically validated, the process continues. In certain embodiments, if the interaction network model does validate, i.e. it is enriched with genes/proteins associated with the disease or query terms being modeled in an independent third party data source, then the interaction network model is used to identify gene/protein nodes that are a component of a known assay and are either (1) genes/proteins recommended from one or more therapeutic experts as biomarkers for the modeled indication, (2) genes/proteins that are significantly associated with the modeled indication (from data mining as described with respect to FIG. 1), or (3) genes/proteins that were added during model construction. At step 325, if the interaction network model cannot be statistically validated, the interaction network model is discarded and the process may start over with step 305. For example, there is no confidence that the interaction network model represents disease biology, so the interaction network model is discarded. In some embodiments, the process may start over again at step 305 by modeling using altered parameters. However, in some instances the problem is not the modeling, it is a lack of evidence/data to build an accurate model.

FIG. 5 depicts a simplified flowchart 500 illustrating a process for biomarker analysis. At step 505, the database terms in subset b and the additional database terms in the interaction network model are ranked as candidate biomarkers. In certain embodiments, a stepwise process may be used to provide a confidence score for candidate biomarkers. The stepwise process may include identifying an intersection between two data sets: a list of database terms (e.g., the database terms in subset b and the additional database terms) such as genes/proteins from the interaction network model and a list of known test analytes having existing validated assays, and ranking the database terms based on the following criteria: Rank 1 candidate biomarkers (i.e. highest confidence candidates), which are those database terms such as genes or proteins independently recommended by one or more therapeutic experts or published industry guidance as a “biomarker” for the interaction network modeled. Rank 2 candidate biomarkers (i.e. lower confidence candidates) meet two criteria: (1) they were identified via data mining, and (2) they are a component of the model (i.e. haven’t been discarded through the modeling process). Rank 3 candidate biomarkers (i.e. lowest confidence candidates) are those database terms such as genes or proteins that are not Rank 1 or Rank 2.

At step 510, for each of the resulting database terms that does not map to existing, validated assays, the database terms may be considered potential biomarkers that would require biological validation, clinical utility, and assay development. At step 515, for each of the resulting database term associations that do map to existing, validated assays, candidate biomarkers with a greatest (e.g., the top 10, 15, 20, or 25 genes or proteins) potential as a biomarker for the specific disease are identified based on the rank of the database term in the models as candidate biomarkers.

III. System Environment

Figure 6:
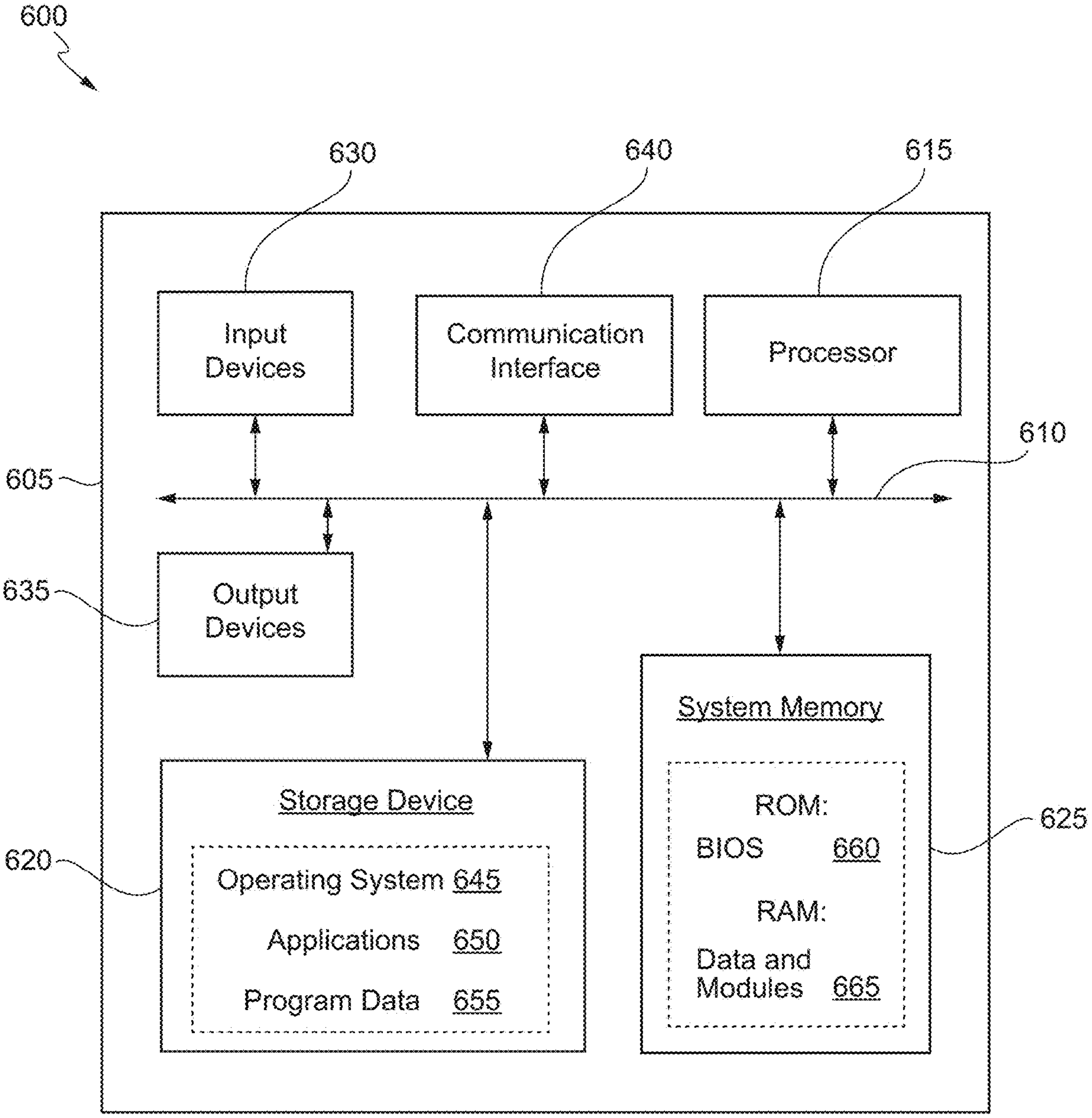
FIG. 6 shows an illustrative architecture of a computing system implemented in accordance with various aspects of the invention.

FIG. 6 is an illustrative architecture of a computing system 600 implemented as some embodiments of the present invention. The computing system 600 is only one example of a suitable computing system and is not intended to suggest any limitation as to the scope of use or functionality of the present invention. Also, computing system 600 should not be interpreted as having any dependency or requirement relating to any one or combination of components illustrated in computing system 600.

As shown in FIG. 6, computing system 600 includes a computing device 605. The computing device 605 can be resident on a network infrastructure such as within a cloud environment, or may be a separate independent computing device (e.g., a computing device of a service provider). The computing device 605 may include a bus 610, processor 615, a storage device 620, a system memory (hardware device) 625, one or more input devices 630, one or more output devices 635, and a communication interface 640.

The bus 610 permits communication among the components of computing device 105. For example, bus 610 may be any of several types of bus structures including a memory bus or memory controller, a peripheral bus, and a local bus using any of a variety of bus architectures to provide one or more wired or wireless communication links or paths for transferring data and/or power to, from, or between various other components of computing device 605.

The processor 615 may be one or more conventional processors, microprocessors, or specialized dedicated processors that include processing circuitry operative to interpret and execute computer readable program instructions, such as program instructions for controlling the operation and performance of one or more of the various other components of computing device 605 for implementing the functionality, steps, and/or performance of the present invention. In certain embodiments, processor 615 interprets and executes the processes, steps, functions, and/or operations of the present invention, which may be operatively implemented by the computer readable program instructions. For example, processor 615 can data mine, e.g., query and/or otherwise obtain or generate a list of database terms from a reference data set including one or more public sources of biomedical text (e.g., peer reviewed literature), scientific abstract, or bioinformatic data, determine a subset b of scrubbed identified database terms based on a score, and generate a list of the subset b. The processor 615 can further develop an interaction network model algorithmically using the subset b of the scrubbed identified database terms and identify candidate biomarkers from the interaction network model. In embodiments, the list of the subset b, the interaction network model, and the list of candidate biomarkers developed by the processor 615 can be stored in the storage device 620.

The storage device 620 may include removable/non-removable, volatile/non-volatile computer readable media, such as, but not limited to, non-transitory machine readable storage medium such as magnetic and/or optical recording media and their corresponding drives. The drives and their associated computer readable media provide for storage of computer readable program instructions, data structures, program modules and other data for operation of computing device 605 in accordance with the different aspects of the present invention. In embodiments, storage device 620 may store operating system 645, application programs 650, and program data 655 in accordance with aspects of the present invention.

The system memory 625 may include one or more storage mediums, including for example, non-transitory machine readable storage medium such as flash memory, permanent memory such as read-only memory (“ROM”), semi-permanent memory such as random access memory (“RAM”), any other suitable type of non-transitory storage component, or any combination thereof. In some embodiments, an input/output system 660 (BIOS) including the basic routines that help to transfer information between the various other components of computing device 605, such as during start-up, may be stored in the ROM. Additionally, data and/or program modules 665, such as at least a portion of operating system 645, program modules, application programs 650, and/or program data 655, that are accessible to and/or presently being operated on by processor 615, may be contained in the RAM. In embodiments, the program modules 665 and/or application programs 650 can comprise a query device or web crawler, the algorithms such as Dikstra's shortest paths, a direct connection algorithm, a growth algorithm to build the interaction network model, a comparison tool, and one or more databases, for example, of known analytical antigens and assays, which provides the instructions and data for execution of the processor 615.

The one or more input devices 630 may include one or more mechanisms that permit an operator to input information to computing device 605, such as, but not limited to, a touch pad, dial, click wheel, scroll wheel, touch screen, one or more buttons (e.g., a keyboard), mouse, game controller, track ball, microphone, camera, proximity sensor, light detector, motion sensors, biometric sensor, and combinations thereof. The one or more output devices 635 may include one or more mechanisms that output information to an operator, such as, but not limited to, audio speakers, headphones, audio line-outs, visual displays, antennas, infrared ports, tactile feedback, printers, or combinations thereof.

The communication interface 640 may include any transceiver-like mechanism (e.g., a network interface, a network adapter, a modem, or combinations thereof) that enables computing device 605 to communicate with remote devices or systems, such as a mobile device or other computing devices such as, for example, a server in a networked environment, e.g., cloud environment. For example, computing device 605 may be connected to remote devices or systems via one or more local area networks (LAN) and/or one or more wide area networks (WAN) using communication interface 640.

As discussed herein, computing system 600 may be configured to identify a biomarker. In particular, computing device 605 may perform tasks (e.g., process, steps, methods and/or functionality) in response to processor 615 executing program instructions contained in non-transitory machine readable storage medium, such as system memory 625. The program instructions may be read into system memory 625 from another computer readable medium (e.g., non-transitory machine readable storage medium), such as data storage device 620, or from another device via the communication interface 640 or server within or outside of a cloud environment. In embodiments, an operator may interact with computing device 605 via the one or more input devices 630 and/or the one or more output devices 635 to facilitate performance of the tasks and/or realize the end results of such tasks in accordance with aspects of the present invention. In additional or alternative embodiments, hardwired circuitry may be used in place of or in combination with the program instructions to implement the tasks, e.g., steps, methods and/or functionality, consistent with the different aspects of the present invention. Thus, the steps, methods and/or functionality disclosed herein can be implemented in any combination of hardware circuitry and software.

IV. Examples

Without intending to limit the scope of the embodiments discussed herein, the systems and methods implemented in various embodiments may be better understood by referring to the following examples.

Example 1

The goal of the following examples were to perform data mining and indication modeling in order to identify: (1) genes associated with chronic obstructive pulmonary disease (COPD), cardiovascular disease (CVD), lung cancer (LC) or tobacco smoke (TS); (2) candidate biomarkers that have existing assays in the Covance Translational Biomarker Solutions (TBS) group that are both associated with a disease indication and tobacco smoke in the lung; and (3) potential biomarkers for assay development (i.e. tests not currently offered by TBS) that are both associated with the disease indication and tobacco smoke in the lung.

Criteria for Relevancy

The approach attempted to find query terms, association words and database terms using a web server in order to identify and enumerate R1, R2, R3 and R4 sentences (R stands for relevancy). An R4 sentence was defined as a sentence that contains just one of the database terms and is used only for statistical normalization. An R3 sentence was defined as a sentence that has one of the database terms as well as the query word. An R2 sentence was defined as a sentence that has one of the database terms, one of the query terms, as well as at least one association word. An R1 sentence was defined as the same as an R2 sentence but in addition, an R1 sentence had to pass pattern recognition criteria. The pattern recognition system was rule based and had been traditionally used to extract protein-protein interactions. Collectively, z-scores for R1, R2, R3 and R4 sentence counts were used to generate a Relevancy Index (RI) score. For the purposes of generating the RI score and calculating Z-scores, R1 sentences were given a value of 50, R2 sentences=25, R3 sentences=5 and R4 sentences=1. The RI score is the sum of the R1, R2, R3 and R4 sentences.

Data Mining Parameters

Initially, MEDLINE (database=PubMed) was data mined for gene-disease or gene-term associations. Specifically, three disease indications were investigated: CVD, COPD, and LC. For COPD, the synonym keywords included: chronic obstructive pulmonary disease; COAD; COLD—chronic obstructive lung disease; COPD; COPD—chronic obstructive pulmonary disease; chronic obstructive airways disease; chronic obstructive lung disease; chronic airflow limitation; chronic airway disease; chronic airway obstruction; chronic irreversible airway obstruction; chronic obstructive airway disease; pulmonary disease, chronic obstructive. For CV, the synonym keywords included: cardiovascular disease; circulatory system disorder; cardiovascular system diseases; circulatory disorders; circulatory disease; circulatory system diseases; diseases of the circulatory system; disorder of the circulatory system; circulatory disorder. For LC, the synonym keywords included: lung cancer; cancer of lung; cancer of the lung; cancer, lung; cancer, pulmonary; lung cancers; malignant lung neoplasm; malignant lung tumor; malignant neoplasm of the lung; malignant tumor of the lung; malignant neoplasm of lung; malignant tumor of lung; pulmonary cancer; pulmonary cancers MEDLINE (database=PubMed) was also data mined for genes associated with the term "tobacco smoke."

All disease indication queries included the filter words: absence; activity; alter; altered; altering; alters; antibodies; antibody; antigen; antigens; associated; association; association; autosomal; biomarker; biomarkers; cause; caused; causes; causing; decline; declined; deficiency; deficient; deleted; diagnosed; diagnosis; dominant; elevate; elevated; enzyme; expressed; expression; gene; genes; involve; involved; involving; lacking; lead; leading; leads; led; linkage; linked; locus; marker; markers; mRNA; mRNAs; mutated; mutation; mutations; observe; observed; observes; observing; polymorphic; polymorphism; polymorphisms; produce; produced; produces; production; protein; proteins; recessive; regulation; relate; related; relates; relating; role; roles; SNP; SNPs. Additionally, text word query included the filter words: gene; genes; protein; proteins. To ensure both current and relevant results, and to optimize data mining time, all queries were restricted to the past 5 years with a limit of 5000 abstracts.

Data Mining Results

All four of the resulting data sets for COPD, CV, LC and TS were cleaned and curated. Specifically, gene names were mapped to Entrez gene IDs and gene symbols using a Disease Associated Gene symbol mappeR (DAGR), which is a custom-built application designed to rapidly map gene symbols to Entrez gene IDs. Manual curation was performed on those associations that failed to be mapped by DAGR. A RI score threshold was assigned based empirically through the development of hundreds of different models. The goal was to use 30-50 high-scoring gene/protein associations as seeds to construct indication models. Specific results are show in Table 1.

TABLE 1

RI score thresholds and resulting gene numbers for gene-disease or gene-term associations.

| Association | RI score threshold | Gene number |
|---|---|---|
| Chronic obstructive pulmonary disease (COPD) | 400 (top score: 2939) | 48 |
| Cardiovascular disease (CVD) | 116 (top score: 890) | 50 |
| Lung cancer (LC) | 347 (top score: 11805) | 49 |
| Tobacco smoke (TS) | 45 (top score: 290) | 50 |

Figure 7A:
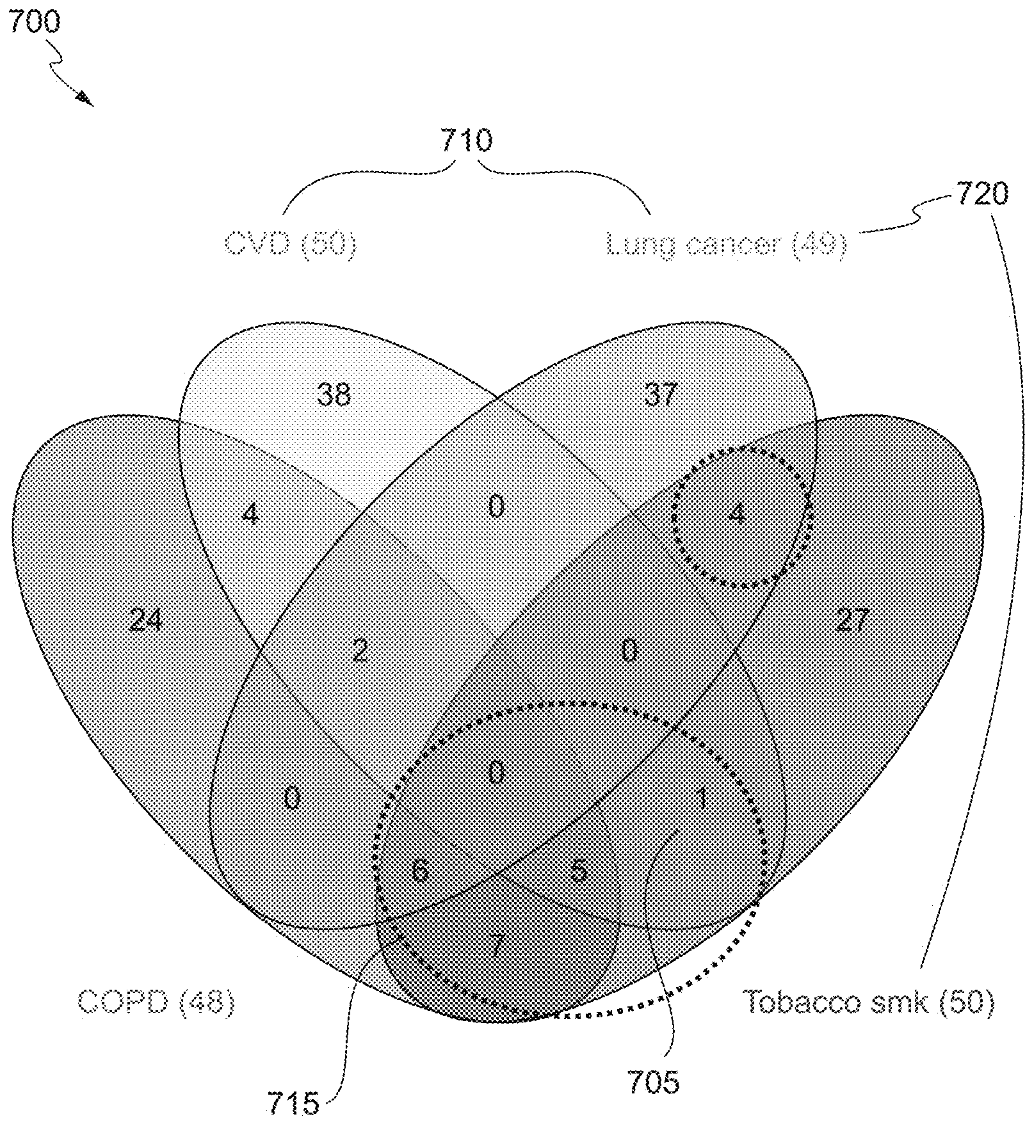
FIGS. 7A and 7B show Venn diagrams of raw data mining results and logical relations between gene sets in accordance with various aspects of the invention.
Figure 7B:
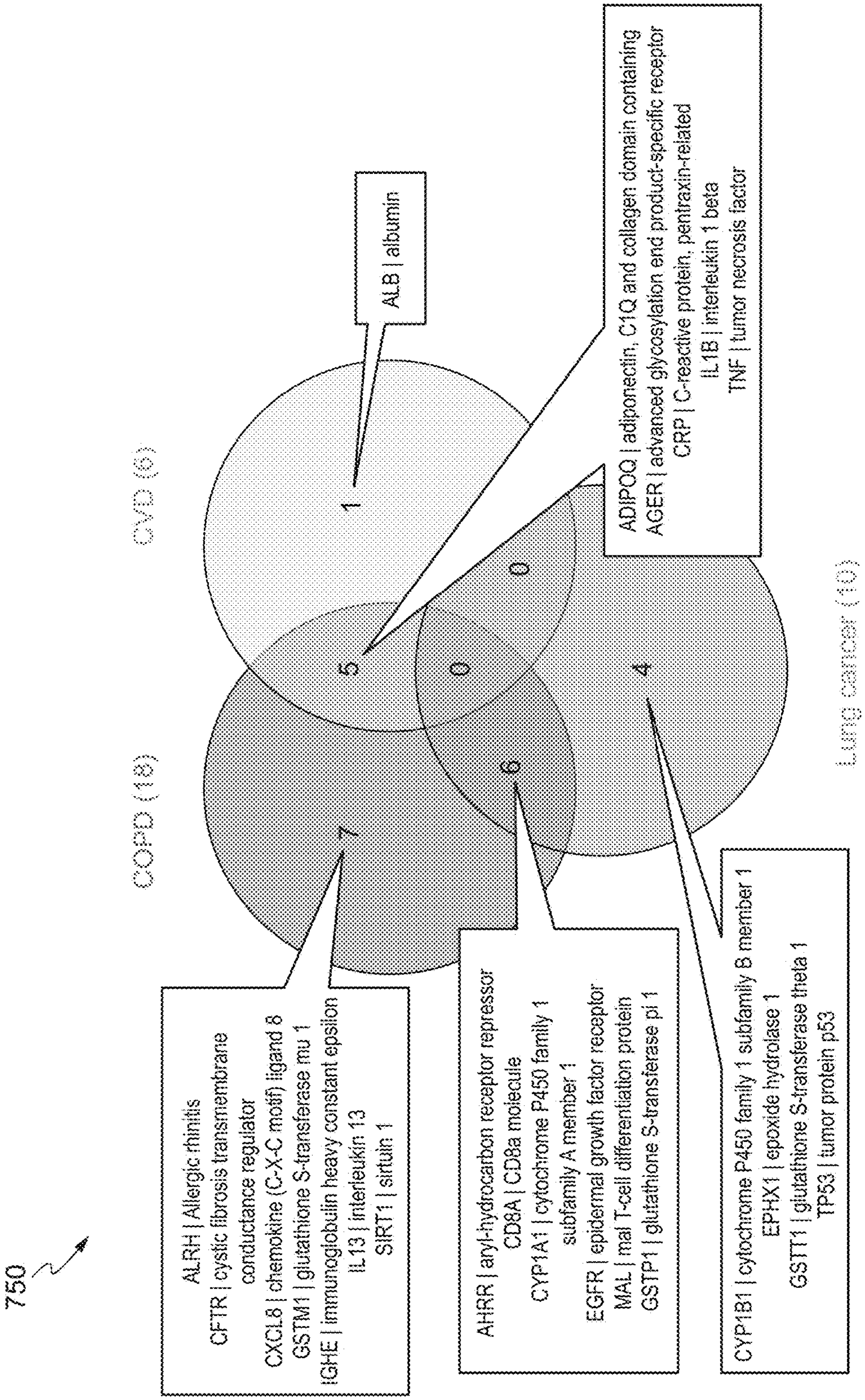

Many genes associated with a given condition overlapped with another condition. In FIGS. 7A and 7B, a Venn diagrams 700 and 750 show logical relations between raw data mining results (i.e., gene sets) for all conditions and the resulting logical relations when associations were restricted to both a disease indication and tobacco smoke. Numbers 705 indicate highly relevant genes associated with each condition 710. FIG. 7A shows raw data mining results compared and the dotted lines 715 indicate those genes at the intersection of COPD, CVD or LC and TS. Numbers 720 are the resulting gene numbers for gene-disease or gene-term associations shown in Table 1. FIG. 7B shows logical relations between gene sets specific to both the indicated disease and tobacco smoke.

Disease Interaction Network Model Construction

Disease models (e.g., gene/protein-gene/protein interaction networks) based on published peer-reviewed research were constructed to simulate disease biology using an integrated software suite for functional analysis of Next Generation Sequencing, variant, CNV, microarray, metabolic, SAGE, proteomics, siRNA, microRNA, and screening data. This step included using an algorithm that calculates the shortest paths (that is, having the smallest possible number of directed one-step interactions) between pairs of initial objects in each direction, for example using the standard Dijkstra's shortest path algorithm (or a similar algorithm for finding the shortest paths between nodes). The resulting output was a single interaction network for each gene set. Each interaction network model was generated tissue specific: COPD, LC and TS models were constructed using only molecules and/or relationships in lung tissue; the CVD model was constructed using only molecules and/or relationships in the cardiovascular system.

The model included genes/proteins and interactions between them (see, e.g., FIG. 4). These genes/proteins included both the initial objects or "seeds" (i.e., genes/proteins identified via data mining) and secondary genes that link the initial objects. Indication modeling simulates the protein-protein interaction "neighborhood" in a specific tissue/organ around genes directly associated with the indication under investigation. As discussed herein, the model was developed algorithmically using Dijkstra's shortest path algorithm (or a similar algorithm for finding the shortest paths between nodes). The process was runs as follows: seed pairs were linked via a tissue/organ specific gene/protein that physically interacts with both seeds. Interactions were based on peer-reviewed study data and specify a direction, mechanism and effect. These "triplets" were constructed over and over for different sets of genes and then pieced together based on an overlap with other triplets. Individual nodes that do not make connections were discarded as well as small-fragment networks and a single large multi-node network was retained. This large, multi-node network is a disease interaction network model that simulates disease biology as it is based on integrated biomedical knowledge accumulated from decades of research data.

Model Validation

The indication modeling is an iterative process that includes validation to ensure the modeling accurately simulates disease biology. A statistical approach was taken to validate the model and verify enrichment of genes from the model in an independent third party data source. The independent third party data source integrates human gene-disease associations from various expert curated databases and text-mining derived associations including Mendelian, complex and environmental diseases. The integration was performed by means of gene and disease vocabulary mapping and by using the independent third party data source association type ontology. The test used was an enrichment analysis to assess whether a data set shows significant over-representation of some biological characteristic. Since the TS model doesn't represent a disease, a similar statistical approach for validation was used but a different publicly available database was used that provides manually curated information about chemical-gene/protein interactions. Specific results of the validation are shown in Table 2.

TABLE 2

Statistical validation results for the simple disease indication models. Source, ID, and indication/interaction name are shown. Enrichment test results are listed as Benjamini and Hochberg False Discovery Rates (FDR (B&H)), a more stringent test than a t-test p-value that controls for the expected proportion of "discoveries" (rejected null hypotheses) that were false (incorrect rejections) (Benjamini and Hochberg, 1995). Genes from input specify the number of model genes in the annotation; genes in annotation specify the number of database genes that map to the indication/interaction.

| Model | Source | ID | Name | FDR (B&II) | Genes from Input | Genes in Annotation |
|---|---|---|---|---|---|---|
| Chronic obstructive Pulmonary disease (COPD) | DisGeNET Curated | umls: C0024117 | Chronic Obstructive Airway Disease | 2.983E−25 | 53 | 497 |
| Cardiovascular disease (CVD) | DisGeNET Curated | umls: C0007222 | Cardiovascular Diseases | 2.087E−22 | 46 | 747 |
| Lung cancer (LC) | DisGeNET Curated | umls: C0024121 | Lung Neoplasms | 9.212E−45 | 81 | 773 |
| Tobacco smoke (TS) | Comparative Toxicogenomics Database | D014028 | Tobacco Smoke Pollution | 3.849E−17 | 60 | 1650 |

Once the disease interaction network model was validated, each indication for association was filtered with tobacco smoke. This was done in a similar manner as shown in FIGS. 7A and 7B for indication gene sets identified via data mining. Specifically, those genes present in both a given disease interaction network model and the TS model were identified. The resulting gene sets included genes associated with both a disease and tobacco smoke in the lung. Once filtered, each condition gene set was then ranked.

Ranking Candidate Biomarkers

A stepwise process was used to provide a confidence score for candidate biomarkers. Rank 1 candidate biomarkers (i.e., highest confidence candidates) were those genes or proteins independently recommended by one or more therapeutic experts as a "biomarker" for the interaction network modeled. Rank 2 candidate biomarkers (i.e. lower confidence candidates) were those genes or proteins identified by data mining and a component of the interaction network model, for example, genes or proteins specific to both the indicated disease and tobacco smoke and identified via MEDLINE data mining (FIGS. 7A and 7B) and in the interaction network model. Rank 3 candidate biomarkers (i.e. lowest confidence candidates) were the genes or proteins that are not Rank 1 or Rank 2, for example, additional genes or proteins obtained via modeling based on triplets (FIG. 4).

Candidate Biomarker Identification

Figure 8:
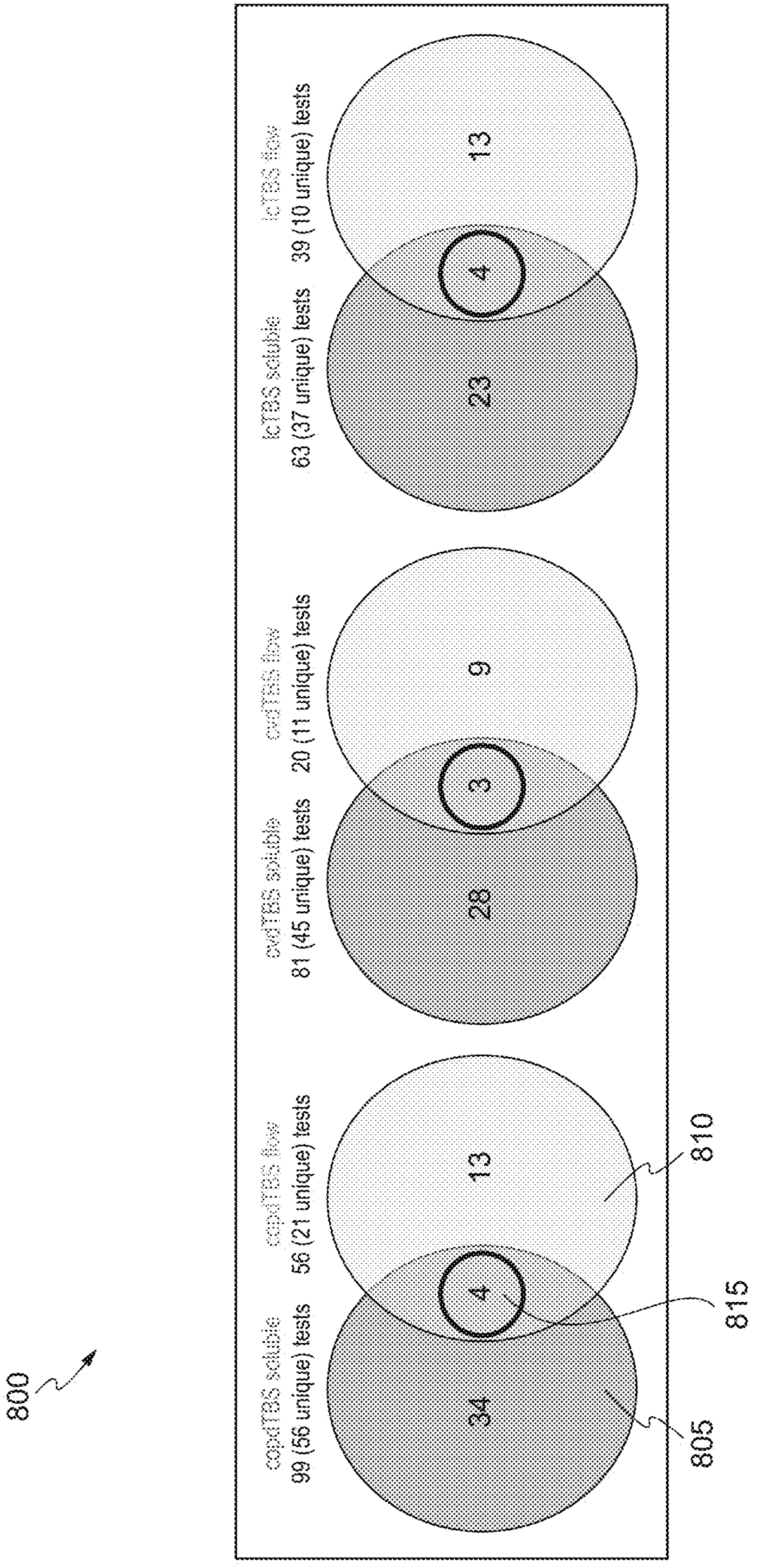
FIG. 8 shows a breakdown of available, validated assays in accordance with various aspects of the invention.

All gene/protein nodes from the interaction network model constructed were mapped to their corresponding Entrez gene IDs and used to identify existing, validated assays in the Covance Translational Biomarker Solutions (TBS) group. Since TBS offers both soluble biomarker and flow cytometry assays, the number of tests available for each condition was broken down accordingly. FIG. 8 shows a breakdown 800 of available, validated TBS assays for each condition. The darker shaded region 805 identifies the number of unique analytes for soluble assays; and the lightly shaded region 810 identifies the number of unique analytes for flow cytometry assays. The number of analytes that have both a soluble and flow cytometry test are circled and shown in the overlapping shaded region 815, and are the same across all conditions (interferon gamma (IFNG), interleukin 2 (IL2), tumor necrosis factor (TNF) and interleukin 4 (IL4) (COPD and LC)). Note that only 11 analytes in total are shared between soluble and flow in the TBS catalog of tests. The total and unique number of tests is shown above each region. The reason for two test counts is that many analytes can be assayed by multiple tests.

Potential Biomarker Identification

Figure 9:
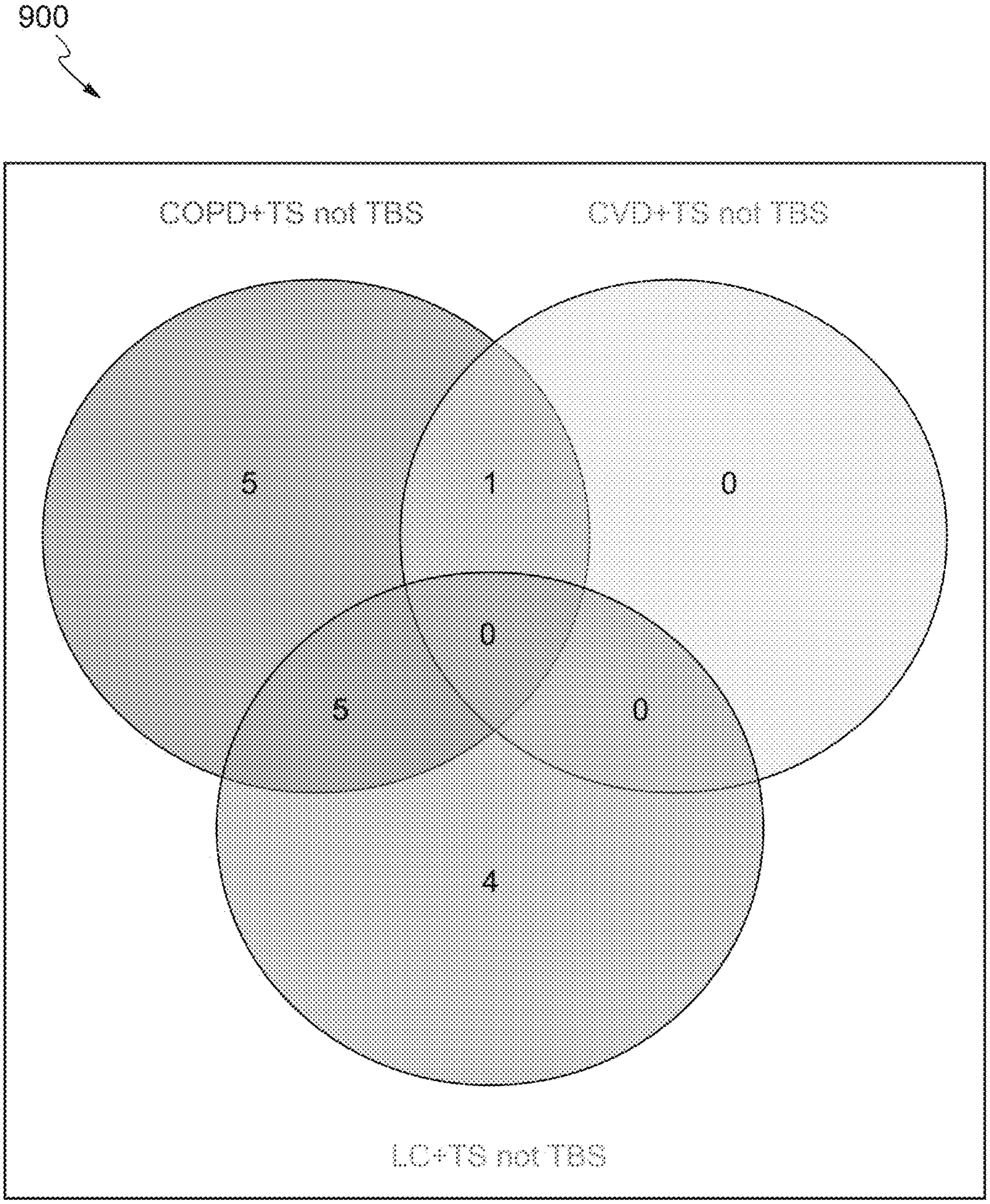
FIG. 9 shows a Venn diagram of logical relations between indication gene sets for potential biomarkers in accordance with various aspects of the invention.

Each of the resulting gene-associations that do not map to existing TBS assays may be considered potential biomarkers that would require assay development. These are genes identified via MEDLINE data mining that are associated with both a disease indication and tobacco smoke, and are components of the interaction network model. Potential biomarkers should be reviewed by TBS scientists for both context and utility. In FIG. 9, a Venn diagram 900 shows logical relations between indication gene sets for potential biomarkers. These are genes identified via MEDLINE data mining that don't map to an available TBS test.

Example 2

The goal of the following examples were to perform data mining and indication modeling in order to identify: (1) genes associated with kidney fibrosis; (2) candidate biomarkers that have existing assays; and (3) potential biomarkers for assay development (i.e. assays not currently offered) that are associated with kidney fibrosis.

Criteria for Relevancy

The approach attempted to find query terms, association words and database terms using a web server in order to identify and enumerate R1, R2, R3 and R4 sentences (R stands for relevancy). An R4 sentence was defined as a sentence that contains just one of the database terms and is used only for statistical normalization. An R3 sentence was defined as a sentence that has one of the database terms as well as the query word. An R2 sentence was defined as a sentence that has one of the database terms, one of the query terms, as well as at least one association word. An R1 sentence was defined as the same as an R2 sentence but in addition, an R1 sentence had to pass pattern recognition criteria. The pattern recognition system was rule based and had been conventionally used to extract protein-protein interactions. Collectively, z-scores for R1, R2, R3 and R4 sentence counts were used to generate a Relevancy Index (RI) score. For the purposes of generating the RI score and calculating Z-scores, R1 sentences were given a value of 50, R2 sentences=25, R3 sentences=5 and R4 sentences=1. The RI score is the sum of the R1, R2, R3 and R4 sentences.

Data Mining Parameters

Initially, MEDLINE (database=PubMed) was data mined for gene-disease or gene-term associations. Specifically, the disease, kidney or renal fibrosis, was investigated. All disease indication queries included the filter words: absence; activity; alter; altered; altering; alters; antibodies; antibody; antigen; antigens; associated; association; association; autosomal; biomarker; biomarkers; cause; caused; causes; causing; decline; declined; deficiency; deficient; deleted; diagnosed; diagnosis; dominant; elevate; elevated; enzyme; expressed; expression; gene; genes; involve; involved; involving; lacking; lead; leading; leads; led; linkage; linked; locus; marker; markers; mRNA; mRNAs; mutated; mutation; mutations; observe; observed; observes; observing; polymorphic; polymorphism; polymorphisms; produce; produced; produces; production; protein; proteins; recessive; regulation; relate; related; relates; relating; role; roles; SNP; SNPs. Additionally, text word query included the filter words: gene; genes; protein; proteins. To ensure both current and relevant results, and to optimize data mining time, all queries were restricted to the past 5 years with a limit of 5000 abstracts. The results identified genes/proteins from peer-reviewed published literature within PubMed associated with kidney or renal fibrosis. Thereafter, text pattern recognition was used to ultimately calculate z-scores for R1, R2, R3 and R4 sentence counts and generate the RI score to measure the strength of association for each of the identified genes/proteins.

Data Mining Results

The resulting data set of identified genes/proteins for kidney fibrosis was cleaned and curated. Specifically, gene names were mapped to Entrez gene IDs and gene symbols using a Disease Associated Gene symbol mappeR (DAGR), which is a custom-built application designed to rapidly map gene symbols to Entrez gene IDs. Manual curation was performed on those associations that failed to be mapped by DAGR. A RI score threshold was assigned based empirically through the development of hundreds of different models. The goal was to use 40-60 high-scoring gene/protein associations as seeds to construct indication models. Specifically, 57 highly relevant genes/proteins were identified from the data mining.

Disease Interaction Network Model Construction

Disease models (e.g., gene/protein-gene/protein interaction networks) based on published peer-reviewed research were constructed to simulate disease biology using an integrated software suite for functional analysis of Next Generation Sequencing, variant, CNV, microarray, metabolic, SAGE, proteomics, siRNA, microRNA, and screening data. This step included using an algorithm that calculates the shortest paths (that is, having the smallest possible number of directed one-step interactions) between pairs of initial objects in each direction, for example using the standard Dijkstra's shortest path algorithm (or a similar algorithm for finding the shortest paths between nodes). The resulting output was a single interaction network for the gene set associated with kidney fibrosis. The interaction network model was generated tissue/organ specific: the model was constructed using molecules and/or relationships in the kidney.

Figure 10:
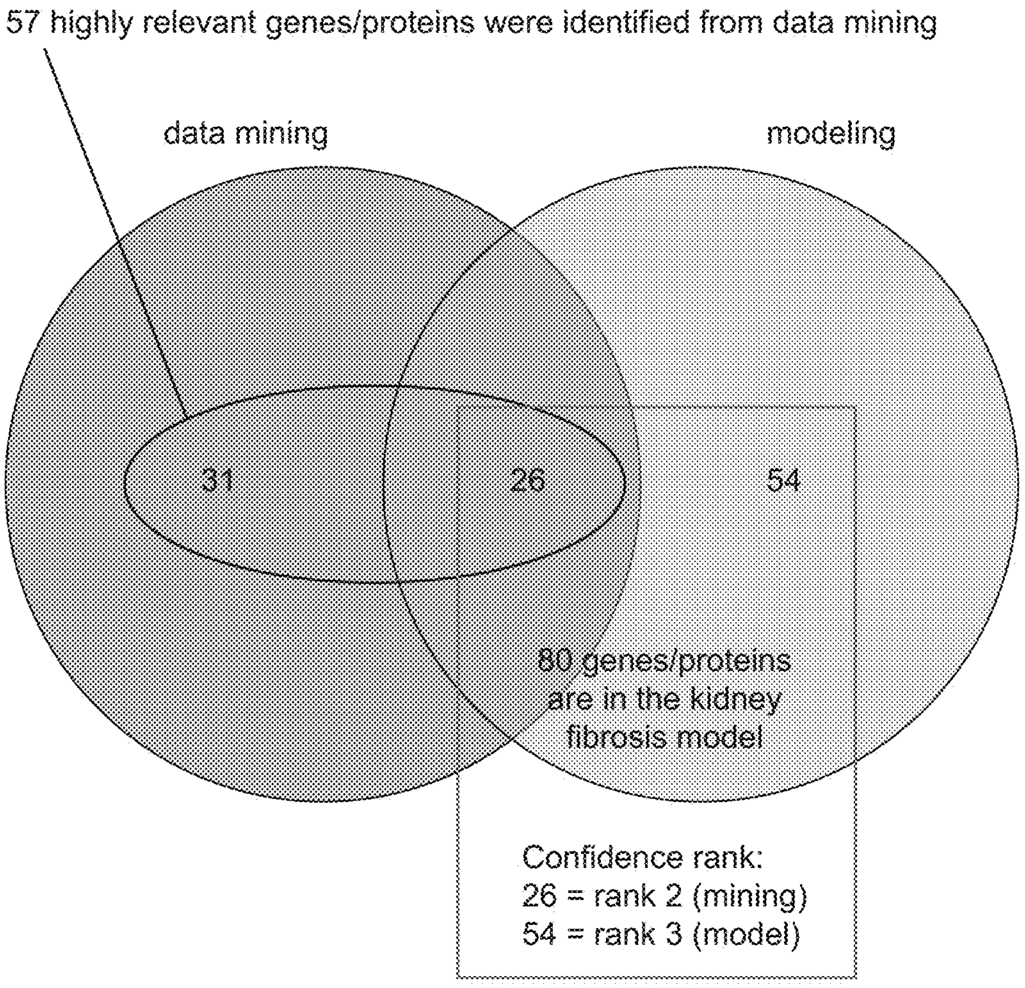
FIG. 10 shows a Venn diagram of data from mining and modeling in accordance with various aspects of the invention.

The model included genes/proteins and interactions between them. These genes/proteins included both the initial objects or "seeds" (i.e., the 57 highly relevant genes/proteins identified from the data mining, which was ultimately restricted to 26 genes/proteins using the tissue/organ based modeling approach) and 54 secondary genes/proteins that were identified by the model alone (see, e.g., the Venn diagram of data from mining and modeling shown in FIG. 10). Additionally, two potential candidate test/biomarkers not genes/proteins but chemicals or small molecules (corticosterone and aldosterone [corticosterone is the precursor molecule to the mineralocorticoid aldosterone, one of the major homeostatic modulators of sodium and potassium levels in vivo]) known to be involved with kidney fibrosis by way of published peer-reviewed research were included in the model.

Figure 11:
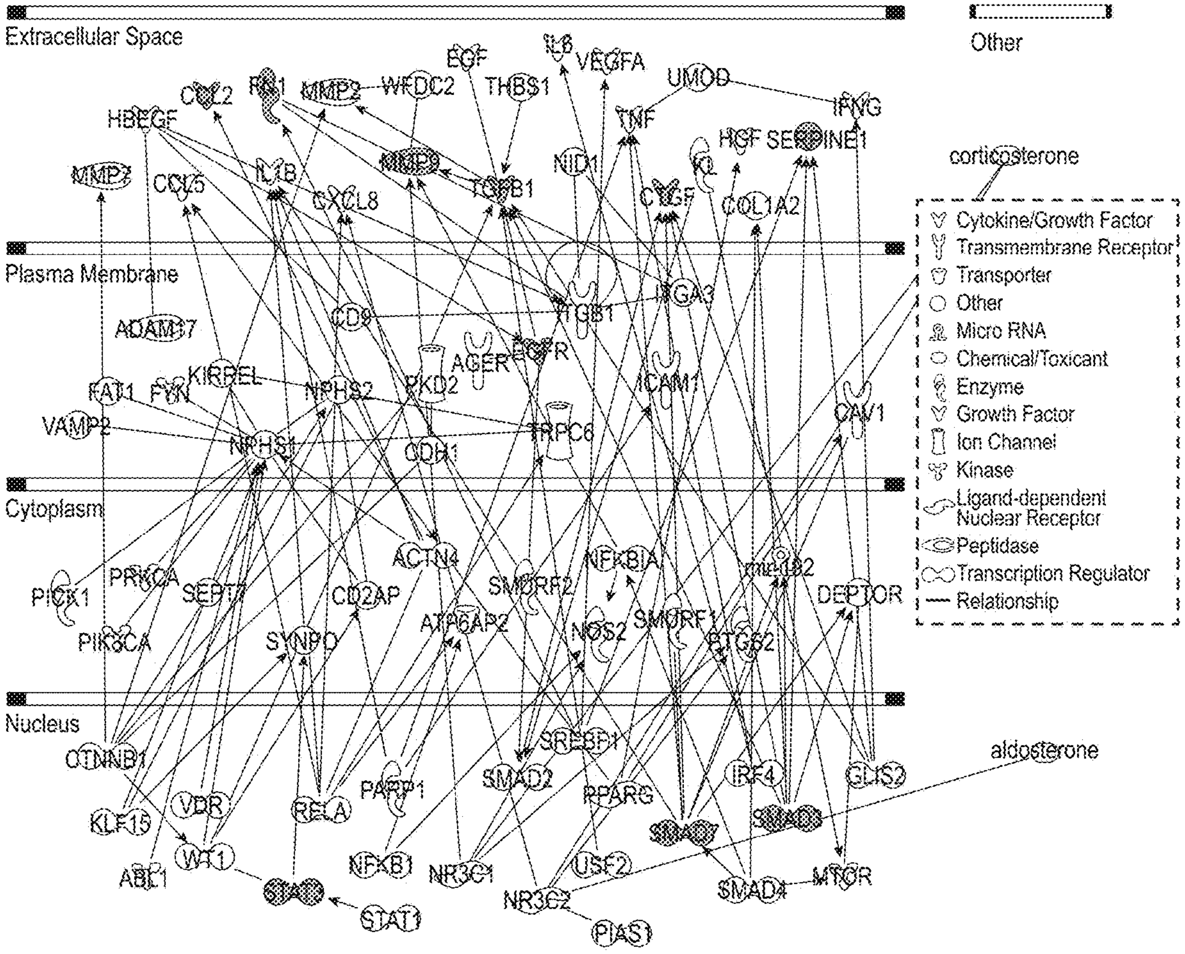
FIG. 11 shows an exemplary multi-node interaction network in accordance with various aspects of the invention.

Indication modeling simulates the protein-protein-chemical (small molecule) interaction "neighborhood" in a specific tissue/organ around genes directly associated with the indication under investigation. As discussed herein, the model was developed algorithmically using Dijkstra's shortest path algorithm (or a similar algorithm for finding the shortest paths between nodes). The process was run as follows: seed pairs were linked via a tissue-specific gene/protein or chemical that physically interacts with both seeds. Interactions were based on peer-reviewed study data and specify a direction, mechanism and effect. These "triplets" were constructed over and over for different sets of genes and then pieced together based on an overlap with other triplets. Individual nodes that do not make connections were discarded as well as small-fragment networks and a single large multi-node network was retained, as shown in FIG. 11 (with top 10 of 26 genes/proteins highlighted from data mining). This large, multi-node network is a disease interaction network model that simulates disease biology as it is based on integrated biomedical knowledge accumulated from decades of research data.

Model Validation

Figure 12:
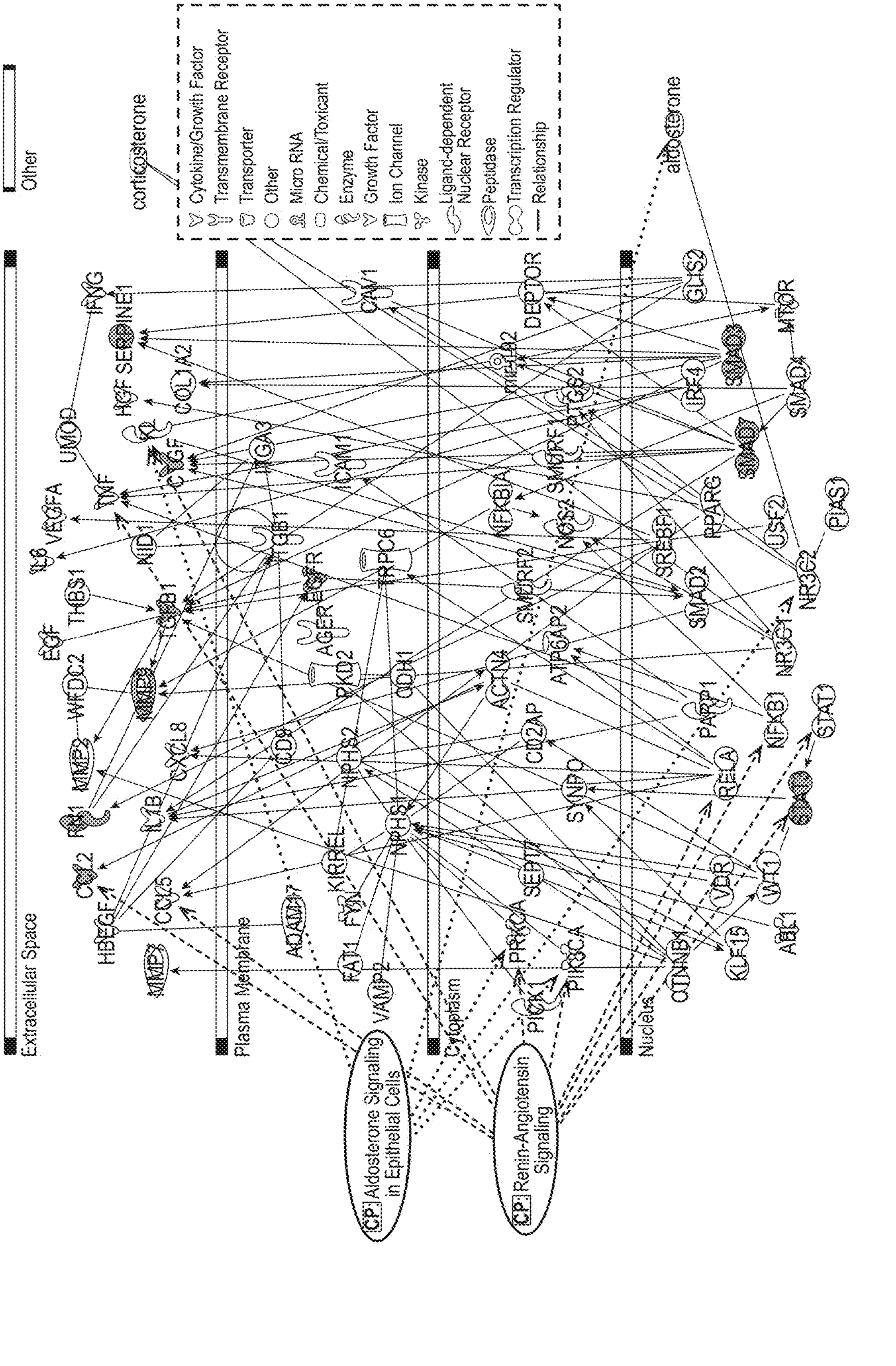
FIG. 12 shows an exemplary multi-node interaction network that highlights known biological pathways providing further confidence to the model validation in accordance with various aspects of the invention.

The indication modeling is an iterative process that includes validation to ensure the modeling accurately simulates disease biology. A statistical approach was taken to validate the model and verify enrichment of genes from the model in an independent third party data source. The independent third party data source integrates human gene-disease associations from various expert curated databases and text-mining derived associations including Mendelian, complex and environmental diseases. The integration was performed by means of gene and disease vocabulary mapping and by using the independent third party data source association type ontology. The test used was an enrichment analysis to assess whether a data set shows significant over-representation of some biological characteristic. As shown in FIG. 12, the indication modeling accurately captured much of the known biological pathways including components of the renin-angiotensin-aldosterone system and aldosterone signaling in epithelial cells, which is indicative of the potential beneficial effects from including the chemicals or small molecules corticosterone and aldosterone in the indication modeling.

Ranking Candidate Biomarkers

A stepwise process was used to provide a confidence score for candidate biomarkers. Rank 1 candidate biomarkers (i.e., highest confidence candidates) were those genes, proteins, or chemicals independently recommended by one or more therapeutic experts as a "biomarker" for the interaction network modeled. Rank 2 candidate biomarkers (i.e. lower confidence candidates) were those genes, proteins, or chemicals identified by data mining and a component of the interaction network model, for example, genes or proteins specific to the indicated disease of renal fibrosis identified via MEDLINE data mining and in the interaction network model. Rank 3 candidate biomarkers (i.e. lowest confidence candidates) were the genes or proteins that are not Rank 1 or Rank 2, for example, additional genes or proteins obtained via modeling based on triplets (FIG. 11).

Candidate Test/Biomarker Identification

Figure 13:
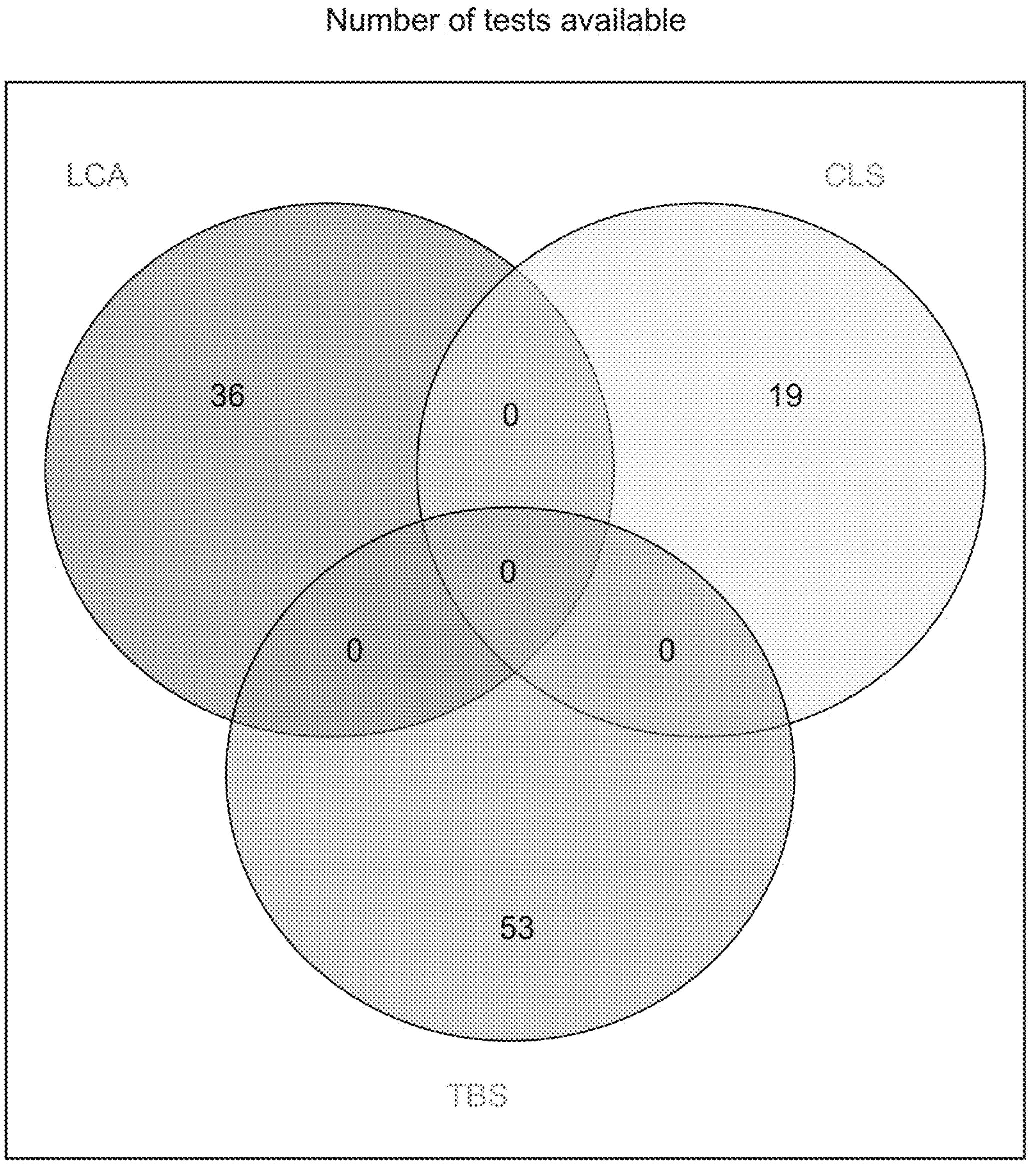
FIG. 13 shows a Venn diagram of tests available in accordance with various aspects of the invention.
Figure 14:
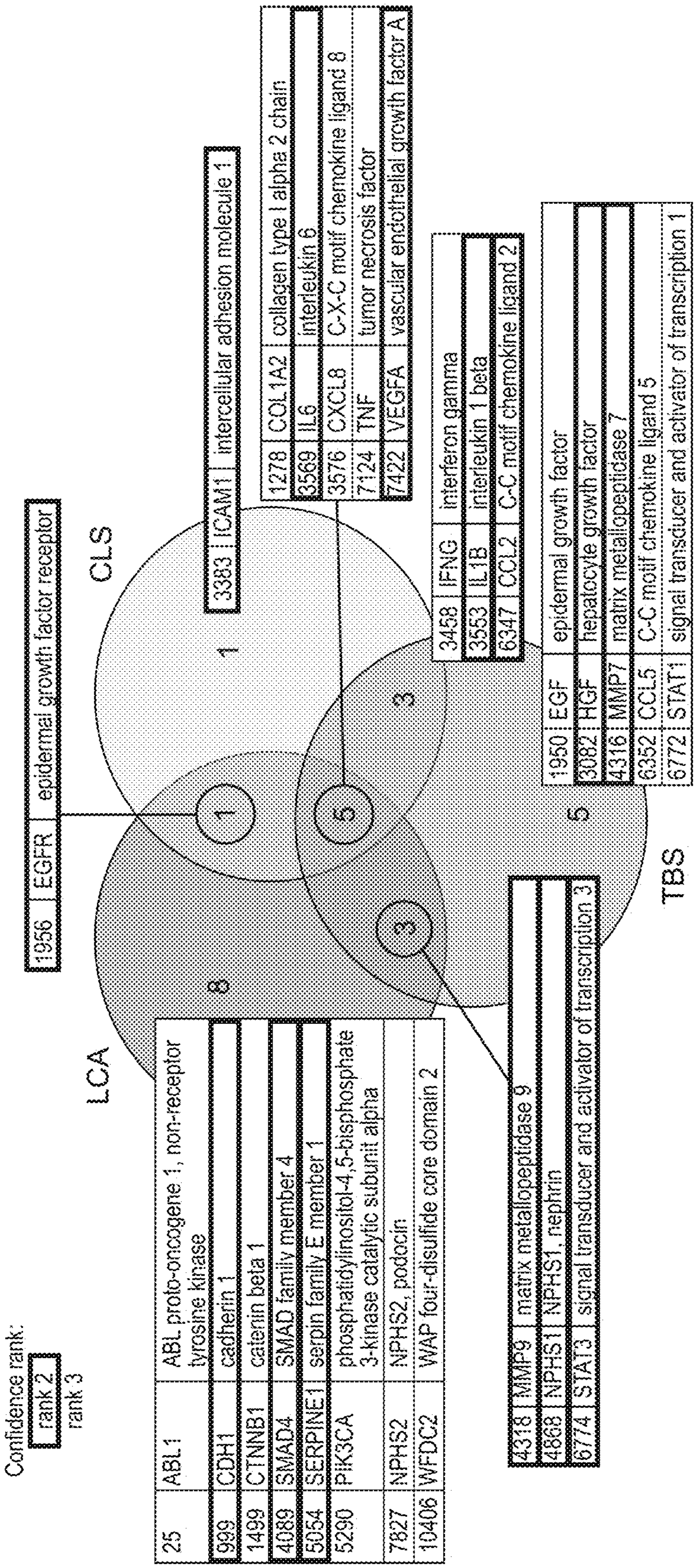
FIG. 14 shows a Venn diagram of candidate biomarkers in accordance with various aspects of the invention.

All gene/protein nodes from the interaction network model constructed were mapped to their corresponding Entrez gene IDs and used to identify existing, validated assays in the Covance Translational Biomarker Solutions (TBS) group, Covance Central Labs (CLS), and LabCorp (LCA). FIG. 13 shows the number of tests available between the three groups. FIG. 14 shows the number of identified biomarkers tested between the three groups with determined confidence ranks assigned for each biomarker. Note that FIG. 14 does not show corticosterone and aldosterone; however, LCA and CLS can test for both.

Potential Biomarker Identification

Each of the resulting gene-associations that do not map to existing assays may be considered potential biomarkers that would require assay development. These are genes identified via MEDLINE data mining that are associated with renal fibrosis. Potential biomarkers should be reviewed by experts or scientists in the field for both context and utility.

While the invention has been described in detail, modifications within the spirit and scope of the invention will be readily apparent to the skilled artisan. It should be understood that aspects of the invention and portions of various embodiments and various features recited above and/or in the appended claims may be combined or interchanged either in whole or in part. In the foregoing descriptions of the various embodiments, those embodiments which refer to another embodiment may be appropriately combined with other embodiments as will be appreciated by the skilled artisan. Furthermore, the skilled artisan will appreciate that the foregoing description is by way of example only, and is not intended to limit the invention.

What is claimed is:

1. A method for identifying a biomarker, the method comprising:

data mining, by a computing device, one or more public sources of biomedical text, scientific abstract, or bioinformatic data using queries to identify database terms associated with one or more predetermined terms;

scoring, by the computing device, association(s) between each of the identified database terms and the one or more predetermined terms;

determining, by the computing device, a subset b based on the score of the association(s) between each of the identified database term and the one or more predetermined terms;

developing, by the computing device, an interaction network model comprising the database terms in subset b, interactions, and additional database terms using a combination of algorithms in a predetermined order, wherein the interaction network model is developed with preset parameters including a tissue or organ specific parameter, which restricts the interactions and the additional database terms to a specific tissue or organ, and wherein the developing comprises:

applying a growth algorithm to the database terms in subset b to build 5-50 nodes upstream including the additional database terms, wherein correlation and expression relationships are excluded in the growth algorithm;

applying a growth algorithm to the database terms in subset b to build 5-50 nodes downstream including the additional database terms, wherein the correlation and expression relationships are excluded in the growth algorithm;

connecting all nodes that can be directly connected given presets parameters using a direct connection algorithm to create a core network, wherein the correlation and expression relationships are excluded in the direct connection algorithm;

applying an algorithm for finding shortest paths between nodes to the core network to identify direct connections and connections where there is one additional step, wherein the correlation and expression relationships are excluded in the algorithm for finding the shortest paths;

applying a direct connection algorithm to all nodes in the core network that can be directly connected given the preset parameters, wherein the correlation and expression relationships are excluded in the direct connection algorithm; and applying the algorithm for finding the shortest paths to the core network to identify direct connections and connections where there is one additional step, wherein the correlation and expression relationships are included in the algorithm for finding the shortest paths; and identifying, by the computing device, candidate biomarkers from the interaction network model based on a ranking of the database terms in subset b and the additional database terms in the interaction network model.

2. The method of claim 1, further comprising:

scrubbing, by the computing device, the identified database terms to remove alleged database terms that are not "actual" database terms of interest to generate a subset a that includes only "actual" database terms of interest; and generating, by the computing device, a list of the subset b that includes a name of the identified database terms, identifiers or symbols of the identified database terms, and the score of the association(s) between each identified database term and the one or more predetermined terms.

3. The method of claim 1, further comprising validating, by the computing device, the interaction network model using a statistical process.

4. The method of claim 3, wherein the validating includes using statistics to demonstrate enrichment of the database terms in subset b and the additional database terms in an independent third party data source that comprises human gene-disease associations.

5. The method of claim 1, further comprising:

identifying, by the computing device, an intersection between a first data set and a second data set, wherein the first data set includes a list of the database terms in subset b and the additional database terms from the interaction network model and a list of known test analytes having existing validated assays; and ranking, by the computing device, the database terms in subset b and the additional database terms as the candidate biomarkers based on criteria including the intersection between the first data set and the second data set.

6. The method of claim 5, wherein the criteria includes: Rank 1 candidate biomarkers, which are those database terms independently recommended by one or more therapeutic experts as a "biomarker"; Rank 2 candidate biomarkers, which are those database terms such as genes or proteins identified by the data mining and a component of the interaction network model; and Rank 3 candidate biomarkers, which are those database terms that are not Rank 1 or Rank 2 candidate biomarkers.

7. The method of claim 1, further comprising:

identifying one or more additional terms to associated with the one or more predetermined terms that were not found in the data mining, and importing, by the computing device, the one or more additional terms into subset b, wherein the interaction network model comprises the database terms and the one or more additional terms in subset b, interactions, and additional database terms.

8. The method of claim 7, wherein the one or more additional terms include chemicals or small molecules involved in one or more biological pathways comprising the database terms.

9. A non-transitory machine readable storage medium having instructions stored thereon that when executed by one or more processors cause the one or more processors to perform a method comprising:

data mining one or more public sources of biomedical text, scientific abstract, or bioinformatic data using queries to identify database terms associated with one or more predetermined terms;

scoring association(s) between each of the identified database terms and the one or more predetermined terms;

scrubbing the identified database terms to remove alleged database terms that are not “actual” database terms of interest to generate a subset a that includes only “actual” database terms of interest;

determining a subset b of the subset a based on the score of the association(s) between each of the identified database term and the one or more predetermined terms;

developing an interaction network model comprising the database terms in subset b, interactions, and additional database terms using a combination of algorithms in a predetermined order, wherein the interaction network model is developed with preset parameters including a tissue or organ specific parameter, which restricts the interactions and the additional database terms to a specific tissue or organ, and wherein the developing comprises:

applying a growth algorithm to the database terms in subset b to build 5-50 nodes upstream including the additional database terms, wherein correlation and expression relationships are excluded in the growth algorithm;

applying a growth algorithm to the database terms in subset b to build 5-50 nodes downstream including the additional database terms, wherein the correlation and expression relationships are excluded in the growth algorithm;

connecting all nodes that can be directly connected given presets parameters using a direct connection algorithm to create a core network, wherein the correlation and expression relationships are excluded in the direct connection algorithm;

applying an algorithm for finding shortest paths between nodes to the core network to identify direct connections and connections where there is one additional step, wherein the correlation and expression relationships are excluded in the algorithm for finding the shortest paths;

applying a direct connection algorithm to all nodes in the core network that can be directly connected given the preset parameters, wherein the correlation and expression relationships are excluded in the direct connection algorithm; and applying the algorithm for finding the shortest paths to the core network to identify direct connections and connections where there is one additional step, wherein the correlation and expression relationships are included in the algorithm for finding the shortest paths; and identifying candidate biomarkers from the interaction network model based on a ranking of the database terms in subset b and the additional database terms in the interaction network model.

10. The non-transitory machine readable storage medium of claim 9, wherein the method further comprises:

scrubbing the identified database terms to remove alleged database terms that are not “actual” database terms of interest to generate a subset a that includes only “actual” database terms of interest; and generating a list of the subset b that includes a name of the identified database terms, identifiers or symbols of the identified database terms, and the score of the association(s) between each identified database term and the one or more predetermined terms.

11. The non-transitory machine readable storage medium of claim 9, wherein the method further comprises validating the interaction network model using a statistical process.

12. The non-transitory machine readable storage medium of claim 11, wherein the validating includes using statistics to demonstrate enrichment of the database terms in subset b and the additional database terms in an independent third party data source that comprises human gene-disease associations.

13. The non-transitory machine readable storage medium of claim 9, wherein the method further comprises:

identifying an intersection between a first data set and a second data set, wherein the first data set includes a list of the database terms in subset b and the additional database terms from the interaction network model and a list of known test analytes having existing validated assays; and ranking the database terms in subset b and the additional database terms as the candidate biomarkers based on criteria including the intersection between the first data set and the second data set.

14. The non-transitory machine readable storage medium of claim 13, wherein the criteria includes: Rank 1 candidate biomarkers, which are those database terms independently recommended by one or more therapeutic experts as a “biomarker”; Rank 2 candidate biomarkers, which are those database terms such as genes or proteins identified by the data mining and a component of the interaction network model; and Rank 3 candidate biomarkers, which are those database terms that are not Rank 1 or Rank 2 candidate biomarkers.

15. The non-transitory machine readable storage medium of claim 9, wherein the method further comprises:

identifying one or more additional terms to associated with the one or more predetermined terms that were not found in the data mining, and importing the one or more additional terms into subset b, wherein the interaction network model comprises the database terms and the one or more additional terms in subset b, interactions, and additional database terms.

16. The non-transitory machine readable storage medium of claim 15, wherein the one or more additional terms include chemicals or small molecules involved in one or more biological pathways comprising the database terms.

17. A system comprising:

one or more processors and non-transitory machine readable storage medium;

program instructions to data mine one or more public sources of biomedical text, scientific abstract, or bioinformatic data using queries to identify database terms associated with one or more predetermined terms;

program instructions to score association(s) between each of the identified database terms and the one or more predetermined terms;

program instructions to scrub the identified database terms to remove alleged database terms that are not "actual" database terms of interest to generate a subset a that includes only "actual" database terms of interest;

program instructions to determine a subset b of the subset a based on the score of the association(s) between each of the identified database term and the one or more predetermined terms;

program instructions to develop an interaction network model comprising the database terms in subset b, interactions, and additional database terms using a combination of algorithms in a predetermined order, wherein the interaction network model is developed with preset parameters including a tissue or organ specific parameter, which restricts the interactions and the additional database terms to a specific tissue or organ, and wherein the developing comprises:

applying a growth algorithm to the database terms in subset b to build 5-50 nodes upstream including the additional database terms, wherein correlation and expression relationships are excluded in the growth algorithm;

applying a growth algorithm to the database terms in subset b to build 5-50 nodes downstream including the additional database terms, wherein the correlation and expression relationships are excluded in the growth algorithm;

connecting all nodes that can be directly connected given presets parameters using a direct connection algorithm to create a core network, wherein the correlation and expression relationships are excluded in the direct connection algorithm;

applying an algorithm for finding shortest paths between nodes to the core network to identify direct connections and connections where there is one additional step, wherein the correlation and expression relationships are excluded in the algorithm for finding the shortest paths;

applying a direct connection algorithm to all nodes in the core network that can be directly connected given the preset parameters, wherein the correlation and expression relationships are excluded in the direct connection algorithm; and applying the algorithm for finding the shortest paths to the core network to identify direct connections and connections where there is one additional step, wherein the correlation and expression relationships are included in the algorithm for finding the shortest paths; and program instructions to identify candidate biomarkers from the interaction network model based on a ranking of the database terms in subset b and the additional database terms in the interaction network model, wherein the program instructions are stored on the non-transitory machine readable storage medium for execution by the one or more processors.

18. The system of claim 17, further comprising:

program instructions to scrub the identified database terms to remove alleged database terms that are not "actual" database terms of interest to generate a subset a that includes only "actual" database terms of interest;

program instructions to generate a list of the subset b that includes a name of the identified database terms, identifiers or symbols of the identified database terms, and the score of the association(s) between each identified database term and the one or more predetermined terms.

19. The system of claim 17, further comprising program instructions to validate the interaction network model using statistics to demonstrate enrichment of the database terms in subset b and the additional database terms in an independent third party data source that comprises human gene-disease associations.

20. The system of claim 17, further comprising:

program instructions to identify an intersection between a first data set and a second data set, wherein the first data set includes a list of the database terms in subset b and the additional database terms from the interaction network model and a list of known test analytes having existing validated assays; and program instructions to rank the database terms in subset b and the additional database terms as the candidate biomarkers based on criteria including the intersection between the first data set and the second data set.

21. The system of claim 17, wherein the criteria includes: Rank 1 candidate biomarkers, which are those database terms independently recommended by one or more therapeutic experts as a "biomarker"; Rank 2 candidate biomarkers, which are those database terms such as genes or proteins identified by the data mining and a component of the interaction network model; and Rank 3 candidate biomarkers, which are those database terms that are not Rank 1 or Rank 2 candidate biomarkers.

22. The system of claim 17, further comprising:

program instructions to identify one or more additional terms to associated with the one or more predetermined terms that were not found in the data mining, and program instructions to import the one or more additional terms into subset b, wherein the interaction network model comprises the database terms and the one or more additional terms in subset b, interactions, and additional database terms.

23. The system of claim 22, wherein the one or more additional terms include chemicals or small molecules involved in one or more biological pathways comprising the database terms.

24. The method of claim 1, further comprising using the identified candidate biomarkers to identify one or more potential disease conditions.

25. The non-transitory machine readable storage medium of claim 9, wherein the method further comprises: using the identified candidate biomarkers to identify one or more potential disease conditions.

26. The system of claim 17, further comprising: program instructions to use the identified candidate biomarkers to identify one or more potential disease conditions.

* * * * *